United States Patent
Wiener et al.

(10) Patent No.: US 7,273,483 B2
(45) Date of Patent: Sep. 25, 2007

(54) APPARATUS AND METHOD FOR ALERTING GENERATOR FUNCTIONS IN AN ULTRASONIC SURGICAL SYSTEM

(75) Inventors: Eitan T. Wiener, Cincinnati, OH (US); William T. Donofrio, Cincinnati, OH (US); Richard F. Schwemberger, Cincinnati, OH (US); Robert P. Gill, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 29 days.

(21) Appl. No.: 09/975,127

(22) Filed: Oct. 10, 2001

(65) Prior Publication Data

US 2002/0161385 A1    Oct. 31, 2002

Related U.S. Application Data

(60) Provisional application No. 60/241,886, filed on Oct. 20, 2000.

(51) Int. Cl.
 *A61B 17/32* (2006.01)
(52) U.S. Cl. .......................... 606/169; 606/170; 604/22
(58) Field of Classification Search ................ 600/461, 600/446, 2, 3, 4, 459–471; 606/167, 169, 606/170, 171; 604/22
See application file for complete search history.

(56) References Cited

U.S. PATENT DOCUMENTS

| | | | |
|---|---|---|---|
| 2,917,691 A | 12/1959 | DePrisco et al. ............ 318/118 |
| 4,811,740 A * | 3/1989 | Ikeda et al. .................. 600/437 |
| 4,868,476 A * | 9/1989 | Respaut ....................... 318/632 |
| 4,897,789 A * | 1/1990 | King et al. ................. 604/6.08 |
| 5,001,649 A | 3/1991 | Lo et al. ..................... 364/484 |
| 5,026,387 A | 6/1991 | Thomas ....................... 606/169 |
| 5,112,300 A | 5/1992 | Ureche ......................... 604/22 |
| 5,180,363 A | 1/1993 | Idemoto et al. ............... 202/32 |
| 5,209,235 A * | 5/1993 | Brisken et al. ............. 600/466 |
| 5,391,144 A * | 2/1995 | Sakurai et al. ................ 604/22 |
| 5,400,267 A * | 3/1995 | Denen et al. ................. 702/59 |
| 5,425,704 A | 6/1995 | Sakurai et al. ................ 604/22 |
| 5,449,370 A | 9/1995 | Vaitekunas .................. 606/169 |
| 5,630,420 A | 5/1997 | Vaitekunas ............. 128/662.03 |
| 5,688,235 A * | 11/1997 | Sakurai et al. ................ 604/22 |
| 5,707,369 A | 1/1998 | Vaitekunas et al. ........... 606/31 |
| 5,879,364 A | 3/1999 | Bromfield et al. .......... 606/169 |
| 5,897,569 A | 4/1999 | Kellogg et al. |

(Continued)

FOREIGN PATENT DOCUMENTS

WO    WO-93/06776 A    4/1993

*Primary Examiner*—Anhtuan T. Nguyen
*Assistant Examiner*—Darwin P Erezo
(74) *Attorney, Agent, or Firm*—Verne E. Kreger, Jr.

(57) ABSTRACT

The present invention provides a system for surgery which includes an ultrasonic hand piece having a end-effector, a console having a digital signal processor (DSP) for controlling the hand piece, and a memory disposed in the end-effector. The generator console sends a drive current to drive the hand piece which imparts ultrasonic longitudinal movement to the blade. As the generator console reads the memory, the hand piece is authenticated for use with the generator console if a copyrighted data string is present in the memory. In a particular embodiment, the data string is an encrypted code, where the hand piece is authenticated for use with the console by decoding a corresponding encryption algorithm resident in the generator console and providing a responding data pattern.

29 Claims, 21 Drawing Sheets

U.S. PATENT DOCUMENTS

| | | |
|---|---|---|
| 5,968,007 A | 10/1999 | Simon et al. .................. 604/22 |
| 6,017,354 A * | 1/2000 | Culp et al. ................... 606/170 |
| 6,019,775 A * | 2/2000 | Sakurai ....................... 606/169 |
| 6,053,871 A * | 4/2000 | Cockburn ................... 600/459 |
| 6,066,135 A * | 5/2000 | Honda ......................... 606/39 |
| 6,090,123 A | 7/2000 | Culp et al. ................... 606/180 |
| 6,237,604 B1 * | 5/2001 | Burnside et al. ............ 128/897 |
| 6,298,255 B1 * | 10/2001 | Cordero et al. ............. 600/372 |
| 6,308,089 B1 * | 10/2001 | von der Ruhr et al. ..... 600/338 |
| 6,331,181 B1 * | 12/2001 | Tierney et al. .............. 606/130 |
| 6,364,839 B1 * | 4/2002 | Little et al. .................. 600/459 |
| 6,434,507 B1 * | 8/2002 | Clayton et al. ............. 702/152 |
| 6,494,882 B1 * | 12/2002 | Lebouitz et al. ............... 606/45 |
| 6,623,423 B2 * | 9/2003 | Sakurai et al. .............. 600/104 |

* cited by examiner

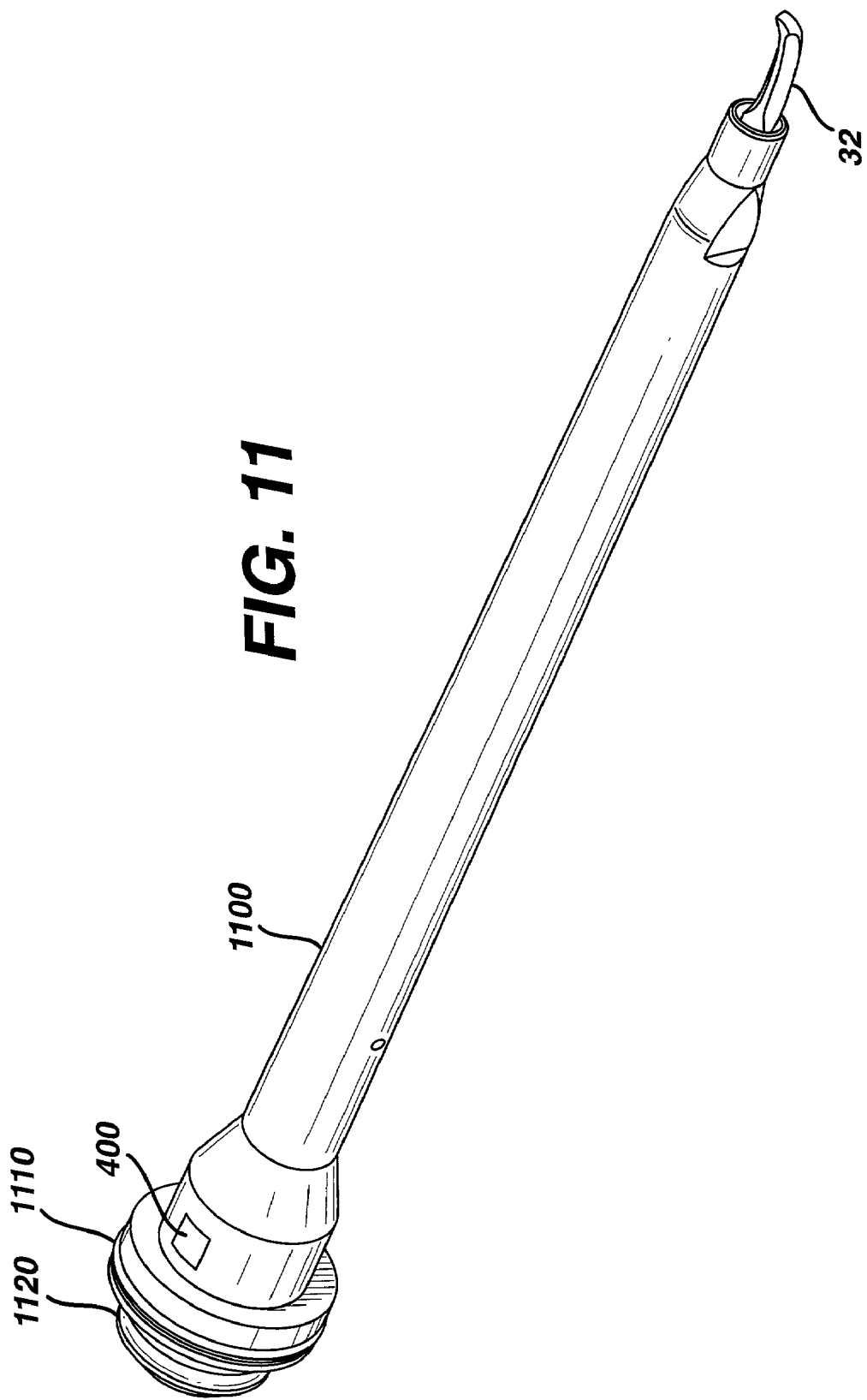

APPARATUS AND METHOD FOR ALERTING GENERATOR FUNCTIONS IN AN ULTRASONIC SURGICAL SYSTEM

RELATED APPLICATIONS

The present invention generally relates to, and claims priority of U.S. Provisional Patent Application 60/241,886 filed on Oct. 20, 2000 and entitled "BLADE IDENTIFICATION IN AN ULTRASONIC SURGICAL HANDPIECE", having a common assignee as the present application, which is incorporated herein by reference.

BACKGROUND OF THE INVENTION

1. Field of the Invention

The present invention generally relates to an apparatus and method for alerting generator functions in an ultrasonic surgical system and more particularly, to an ultrasonic surgical system for providing information to a generator from an ultrasonic surgical instrument.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop that includes a voltage controlled oscillator, a frequency divider, a power switch, a match net and a phase detector, stabilizes the frequency applied to the hand piece. A microprocessor controls the amount of power by sampling the frequency current and voltage applied to the hand piece, because these parameters change with load on the blade.

The power versus load curve in a generator in a typical ultrasonic surgical system, such as that described in the Thomas patent has two segments. The first segment has a positive slope of increasing power, as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, keeps monitoring of the transducer current to voltage phase angle and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot hop over other resonance modes or make any heuristic decisions such as what resonance/s to skip or lock onto and ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

However, the prior art systems do not provide for authentication of the use of the hand piece with the generator console. Furthermore, conducting diagnostic and performance tests in the prior art systems is cumbersome. Reprogramming or upgrading of the console in the prior art systems is also burdensome, since each console needs to be independently tested and upgraded. In addition, the prior art system do not allow operation of the console with varied driving current and output displacement, depending on the type and output ability of hand piece in operation with the console. Therefore, there is a need in the art for an improved system for implementing surgical procedures which overcomes these and other disadvantages in the prior art.

SUMMARY OF THE INVENTION

The present invention provides a system for implementing surgical procedures which includes an ultrasonic surgical hand piece having an end-effector, a generator console having a digital signal processor (DSP) for controlling the hand piece, and a memory device such as an EEPROM (Electrically Erasable Programmable Read Only Memory) disposed in the sheath of the end-effector or in the handle, grip, or mount portion of shears or scissors or forceps. A data string, which identifies the hand piece and generator performance characteristics, is stored in the memory device. During initialization of the system and/or periodically during standby or ready or while in use, the generator console sends an interrogation signal to the hand piece to obtain a readout of the memory. As the generator console reads the memory, the hand piece blade or shears is authenticated for use with the generator console if the proper data string is present. The hand piece blade or shears is not authenticated for use with the console if the data string is not present or is not correct. In a particular embodiment of the invention, the data string is an encrypted code, where the hand piece or blade or shears is authenticated for use with the generator console by decoding a corresponding encryption algorithm resident in the console and providing a responding data pattern.

Moreover, to prevent errors in operating the hand piece or blade or shears, the memory can store certain diagnostic information which the generator console can utilize in determining whether the operation of the hand piece should be handicapped or disabled or alert an end user without handicap-or disable-mode operations. For instance, the memory can store information such as limits on the time that the hand piece is active, the number of activations within a time period, the number of defective blades used, operating temperature, maximum allowable rate of change in temperature, and other limits. Those limits stored in the memory can be re-initialized accordingly based on various operational conditions of the hand piece.

The memory can also be used to reprogram or upgrade the generator console, if needed. For example, new hand pieces are issued periodically as new system functionality is achieved. When such a new hand piece is connected, the system perform diagnostic tests to determine whether a reprogram or upgrade of the generator console is needed. If it is determined that a reprogram or upgrade is needed, the generator console reads the memory located in the sheath of the end-effector of the hand piece where a reprogram or upgrade code is stored. Using the reprogram or upgrade code read from the memory, the generator console is reprogrammed or upgraded accordingly. Therefore, the generator consoles in the field can be upgraded automatically without having to return them to the manufacturer or to send a service technician to the generator console. Alternately, rather than reprogramming the generator memory, the blade/shear memory data is utilized by the generator console as the basis for operation parameters for the particular blade/shear in use. Default parameters are reverted to in operating the hand piece when particular parameters are not present in subsequent blades/shears attached to handpiece.

The memory can also store energy level information and corresponding output displacement for driving the particular hand piece. By reading the energy level information, the generator console can drive the hand piece according to the output displacement which is best for that hand piece and/or blade/shears.

In addition, the memory can store frequency sweep information including the nominal resonant frequency, and start and stop sweep points for effecting a frequency sweep.

Upon reading of the frequency sweep information stored in the memory, the generator console effects a frequency sweep in the indicated frequency range for detecting a resonant frequency for operating the hand piece. In addition, the memory can store frequencies or frequency ranges that should not be swept, such as frequencies that are or tend to be transverse-resonant which should be avoided. These stored frequencies can be in the wider specified sweep range allowed, which is stored in the blade/shear memory.

In accordance with the invention, a method is provided for implementing procedures in a system including an ultrasonic surgical hand piece having a end-effector, a console having a digital signal processor (DSP) for controlling the hand piece, and a memory disposed in the sheath of the end-effector in or attached to the hand piece. The method according to the invention includes reading information stored in the memory, determining whether a particular data string is present in the memory, authenticating use of the hand piece or blade or shear with the console if the data string is present, sending a drive current to drive the hand piece, and imparting ultrasonic movement to the end-effector of the hand piece according to information in the memory. In a particular embodiment, the method according to the invention also includes decoding an encryption algorithm in the generator console, and providing a responding data pattern, where the data string is an encrypted code.

In a further embodiment, the method according to the invention includes instructing the hand piece to operate in a handicap mode if the temperature of the hand piece exceeds a handicap limit, and disabling the hand piece if the temperature of the hand piece exceeds a disable limit. The method according to the invention can also include instructing the hand piece to operate in a handicap mode if the number of defective blades found in a time period of operating the hand piece exceeds a handicap limit, and disabling the hand piece if the number of defective blades found in the time period exceeds a disable limit. The method according to the invention can further include instructing the hand piece to operate in a handicap mode if the time the hand piece has been active exceeds a handicap limit, and disabling the hand piece if the number of defective blades found in the time the hand piece has been active exceeds a disable limit. The method according to the invention can include further steps of instructing the hand piece to operate in a handicap mode if the number of activations for the hand piece within a time period exceeds a handicap limit, and disabling the hand piece if the number of activations for the hand piece within the time period exceeds a disable limit. The handicap and disable limits stored in the memory can be re-initialized based on varied operational conditions of the hand piece.

In an additional embodiment, the method according to the invention also includes determining whether a reprogramming or upgrade of the generator console is needed, reading a reprogram or upgrade code stored in the memory and reprogramming the generator console using the reprogram or upgrade code, if it is determined that a reprogram or upgrade of the generator console is needed.

Moreover, the method according to another embodiment of the invention further includes reading energy level information stored in the memory, and driving the hand piece according to a corresponding output displacement, where the energy level information stored in the memory is correlated with corresponding output displacement for driving the particular hand piece or blade or shears. In yet another embodiment, the method according to the invention also includes reading a nominal resonant frequency, a start sweep point and a stop sweep point delimiting a frequency range from the memory, effecting a frequency sweep in the frequency range, and detecting a resonant frequency for operating the hand piece. Alternatively, the frequency range information stored in the memory can be a nominal resonant frequency, a bias amount and a margin amount, where the frequency range for the frequency sweep is calculated based on the nominal resonant frequency, the bias amount and the margin amount. In addition, frequencies or frequency bands to be avoided in the sweeping or driving, or the transverse resonant frequencies, can be stored for use by the generator to operate the handpiece or portion diagnostics.

BRIEF DESCRIPTION OF THE DRAWINGS

The foregoing and other advantages and features of the invention will become more apparent from the detailed description of the preferred embodiments of the invention given below with reference to the accompanying drawings (not necessarily drawn to scale) in which:

FIG. 11 is an isometric view of a portion of the ultrasonic surgical hand piece with a non-volatile memory in the end-effector in accordance with the invention;

DETAILED DESCRIPTION OF THE PREFERRED EMBODIMENTS

Figure 1:
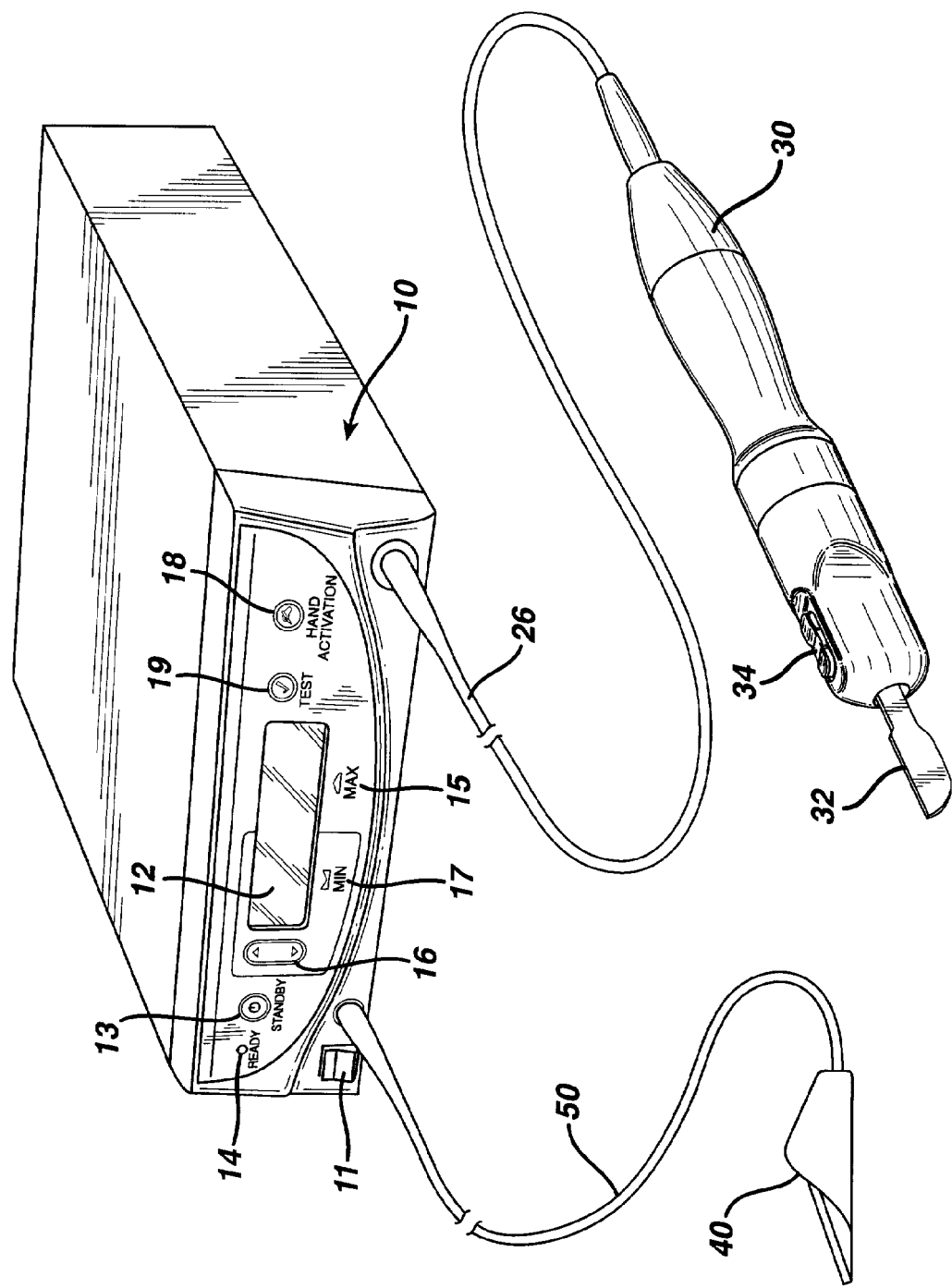
FIG. 1 is an illustration of a console for an ultrasonic surgical cutting and hemostasis system, as well as a hand piece and foot switch in which the method of the present invention is implemented.

FIG. 1 is an illustration of a system for implementing surgical procedures according to the invention. By means of a first set of wires in cable 26, electrical energy, i.e., drive current, is sent from the generator console 10 to a handpiece 30 where it imparts ultrasonic longitudinal movement to a surgical device, such as a sharp end-effector 32. This blade can be used for simultaneous dissection and cauterization of tissue. The supply of ultrasonic current to the hand piece 30 may be under the control of a switch 34 located on the hand piece, which is connected to the generator in the generator console 10 via wires in cable 20. The generator may also be controlled by a foot switch 40, which is connected to the generator console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. This automatically deactivates the MAX button. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate or force applied by the surgeon to the blade, the nature of the tissue type and the vascularity of the tissue.

Figure 2:
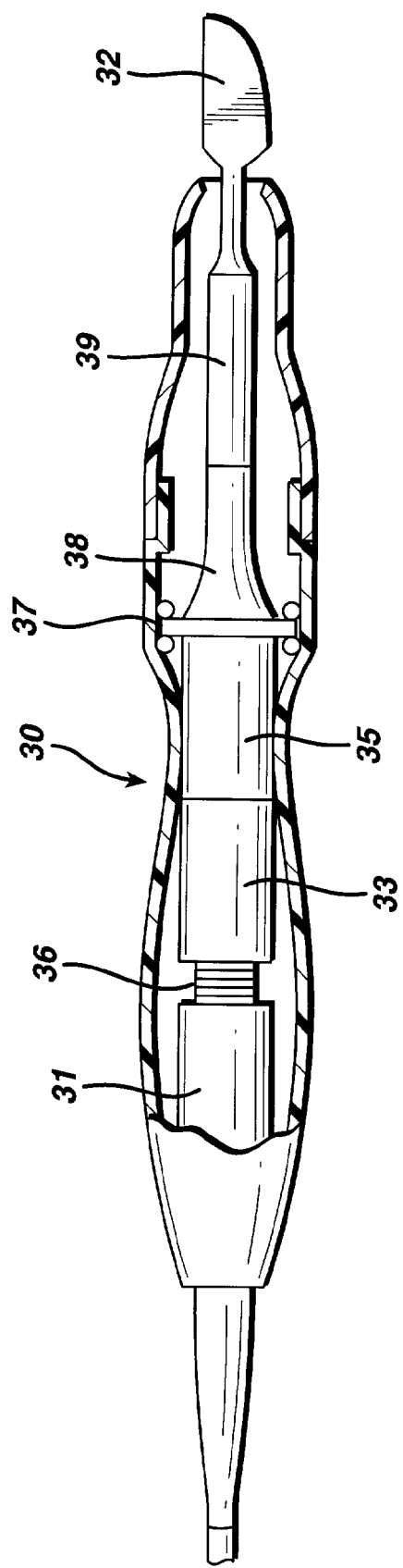
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven at maximum current at the transducer's resonant frequency. However, the current providing the maximum motion will vary with each hand piece and is a value stored in the non-volatile memory of the hand piece so the system can use it.

The parts of the hand piece are designed such that the combination will oscillate at the same resonant frequency. In particular, the elements are tuned such that the resulting length of each such element is one-half wavelength or a multiple thereof. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion from 20 to 25 microns at the transducer stack is amplified by the horn 38 into blade movement of about 40 to 100 microns.

Figure 3A:
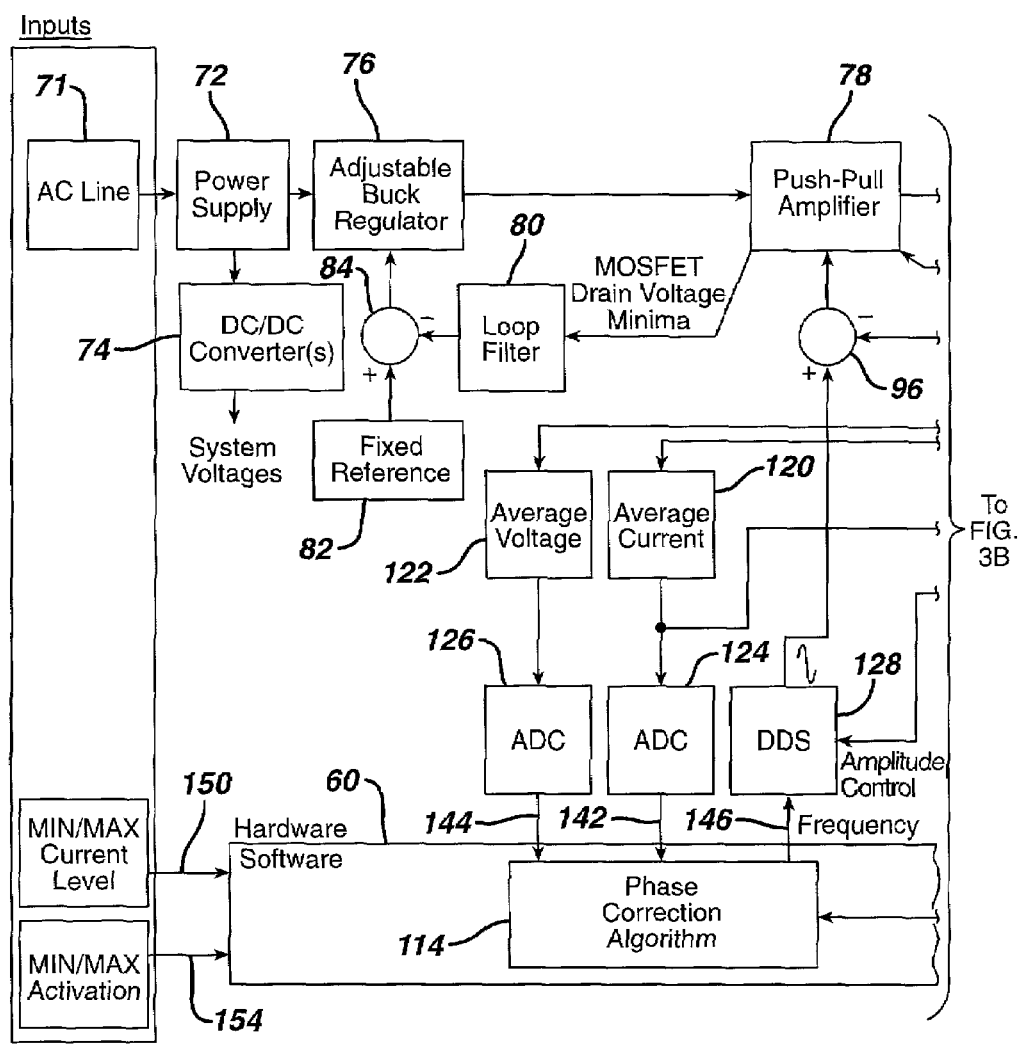
FIG. 3A and FIG. 3B are block diagrams illustrating the ultrasonic according to an embodiment of the invention.
Figure 3B:
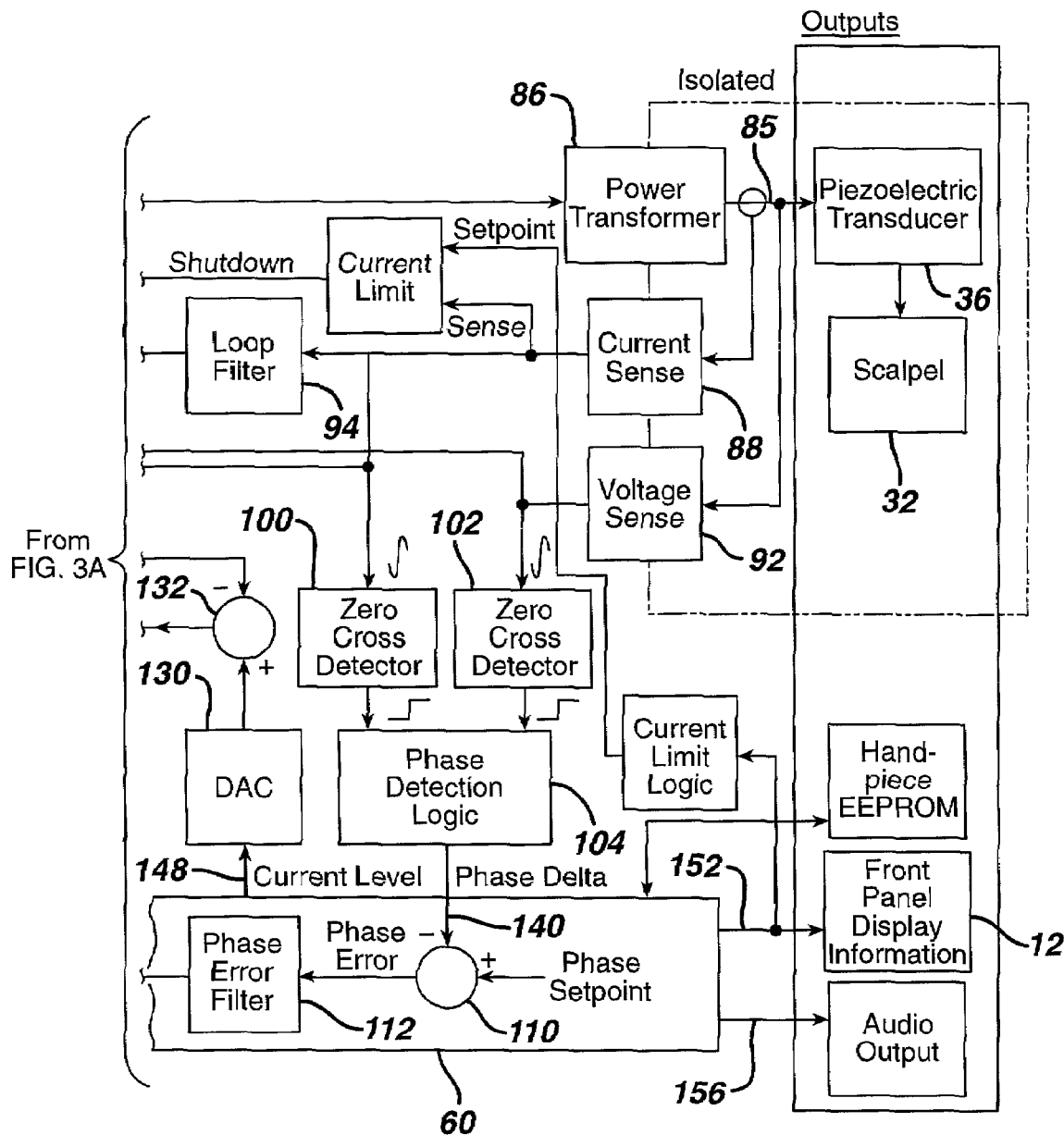

The system which creates the ultrasonic electrical signal for driving the transducer in the hand piece is illustrated in FIG. 3A and FIG. 3B. This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3B) to the console front panel display 12.

To actually cause the surgical blade to vibrate, the user activates the foot switch 40 or the hand piece switch 34. This activation puts a signal on line 154 in FIG. 3A. This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

In order to obtain the impedance measurements and phase measurements, the DSP 60 and the other circuit elements of FIGS. 3A and 3B are used. In particular, push-pull amplifier 78 delivers the ultrasonic signal to a power transformer 86, which in turn delivers the signal over a line 85 in cable 20 to the piezoelectric transducers 36 in the hand piece. The current in line 85 and the voltage on that line are detected by current sense circuit 88 and voltage sense circuit 92. The current and voltage sense signals are sent to average voltage circuit 122 and average current circuit 120, respectively, which take the average values of these signals. The average voltage is converted by analog-to-digital converter (ADC) 126 into a digital code that is input to DSP 60. Likewise, the current average signal is converted by analog-to-digital converter (ADC) 124 into a digital code that is input to DSP 60. In the DSP the ratio of voltage to current is calculated on an ongoing basis to give the present impedance values as the frequency is changed. A significant change in impedance occurs as resonance is approached.

The signals from current sense 88 and voltage sense 92 are also applied to respective zero crossing detectors 100, 102. These produce a pulse whenever the respective signals cross zero. The pulse from detector 100 is applied to phase detection logic 104, which can include a counter that is started by that signal. The pulse from detector 102 is likewise applied to logic circuit 104 and can be used to stop the counter. As a result, the count which is reached by the counter is a digital code on line 104, which represents the difference in phase between the current and voltage. The size of this phase difference is also an indication of resonance. These signals can be used as part of a phase lock loop that cause the generator frequency to lock onto resonance, e.g., by comparing the phase delta to a phase set point in the DSP in order to generate a frequency signal to a direct digital synthesis (DDS) circuit 128 that drives the push-pull amplifier 78.

Further, the impedance and phase values can be used as indicated above in a diagnosis phase of operation to detect if the blade is loose. In such a case the DSP does not seek to establish phase lock at resonance, but rather drives the hand piece at particular frequencies and measures the impedance and phase to determine if the blade is tight.

The transducer drive circuitry of power transformer 86 shown in FIG. 3B may be represented by an equivalent electrical circuit having components Co, Ls, Cs, and Rs which form a transducer equivalent circuit Tequiv, where Co is a shunt capacitance and represents the electrical capacitance of the piezoelectric elements of the piezoelectric transducer 36 shown in FIG. 2.

Ls, Cs and Rs form an electrical equivalent of the overall mechanical system and collectively represent the mechanical branch. Ls is the effective mass of the system, Cs is the effective compliance and Rs represents mechanical losses associated with friction, internal material dissipation and/or the power delivered to the tissue.

An Inductor Lt is also provided and is matched to the shunt capacitance Co at the resonance of the ultrasonic system, such as approximately 55.5 kHz. Hence, Lt and Co electrically cancel each other at the resonant frequency. As a result, all of the drive current will flow through the mechanical branch. This helps to ensure that the ultrasonic excursion of the transducer is primarily proportional to the drive current.

Two resistors Rp/2 sum in series to a resistance of Rp. This resistance helps to establish an upper limit of the overall impedance of the output circuit, and also establishes an upper limit for the drive voltage. In preferred embodiments, Rp is a relatively large resistance. At resonance, the parallel combination of Rp and Rs is effectively Rs, because Rs is much smaller then Rp, even when coagulating and cutting tissue.

A series combination of capacitors Cv1 and Cv2 is used to form a voltage divider. Together these capacitors reduce the high voltage that typically drives the transducer to a level which is appropriate for signal processing by integrated circuits (not shown). A transformer Vt couples the reduced voltage to the feedback circuitry (voltage sense 92 of FIG. 3B) and also provides isolation between the drive circuitry and the other circuitry of the generator.

A small voltage drop is provided across a series combination of resistors R3 and R4. In the preferred embodiment, the series combination is a relatively low resistance in the order of ohms. The voltage drop across R3 and R4 is proportional to the drive current. This voltage is provided to the feedback circuitry (current sense 88 of FIG. 3B) through a transformer IT, which also isolates the drive circuitry from the rest of the circuitry of the generator. This signal represents current in the control algorithms implemented in the generator.

A pair of resistors R1, R2 is used to establish a minimum impedance level to the control circuitry for use in the control algorithms. The resistance is divided between two output arms Vout1, Vout2 of the power transformer to help mitigate electromagnetic radiation and leakage current.

Figure 4:
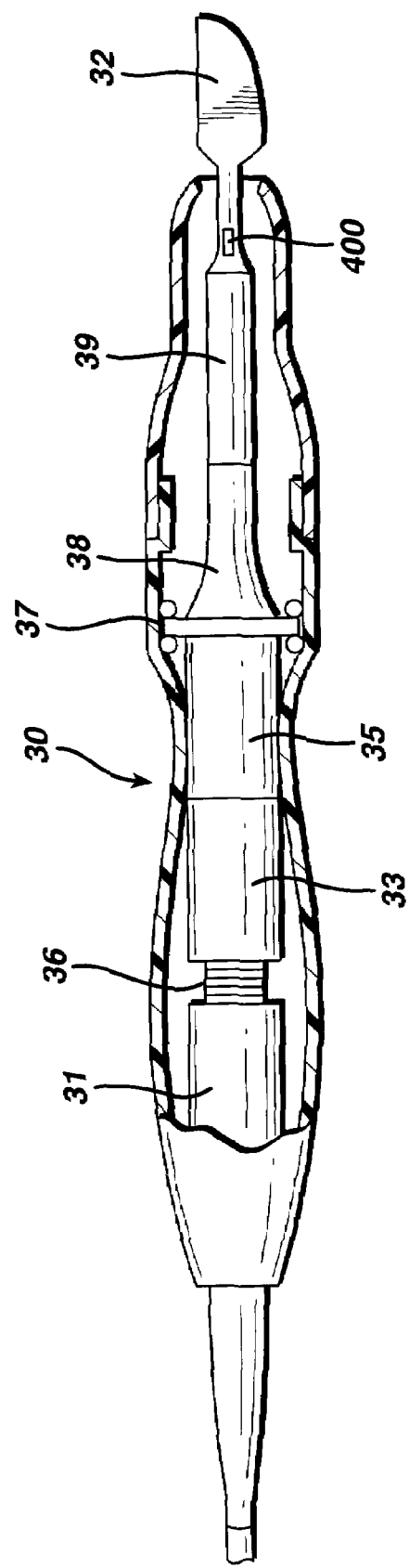
FIG. 4 is a diagram that illustrates a non-volatile memory in the sheath of the end-effector in the ultrasonic surgical hand piece according to the invention.

FIG. 4 is a diagram that illustrates a non-volatile memory 400 in the sheath of the end effector according to the invention. The memory 400 is advantageously provided in the sheath of the end-effector for reducing unneeded complexity in electrical isolation configurations which contribute to increases in costs, complications in cross-talk noise issues, and adversely affects the ergonomic performance of the hand piece 30. By placing the memory 400 in the sheath of the end-effector, adequate electrical isolation of the circuitry in the memory 400 from the hand piece 30, the human operator thereof, and the patient is readily achieved. Also, the number of wires in cable 26 can be reduced.

Figure 4B:
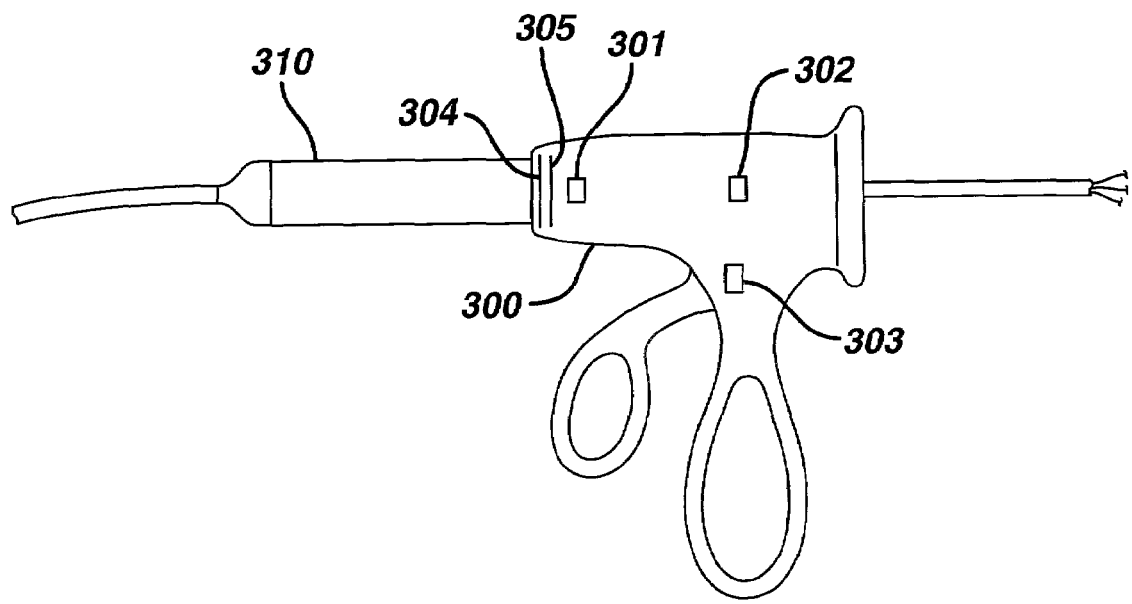
FIG. 4B is a diagram that illustrates a non-volatile memory in the handle/grip/mount portion (non-sheath portion) of ultrasonic shears according to the invention.

FIG. 4B is a diagram that illustrates a non-volatile memory 303 in the grip portion of shears 300 according to the invention. Alternate or additional locations for memory are also shown as memory 301 located in the mount portion and/or memory 302 in the grip portion of shears 300. The shears 300 is attached to handpiece 310. The contacts 304 and 305 are resident within, outside, or embedded into the shears mount or grip vicinity and are wired to the memory. These contacts make connection with corresponding contacts within or on the handpiece to permit generator communications through the handpiece to the memory in the shears.

Figure 5:
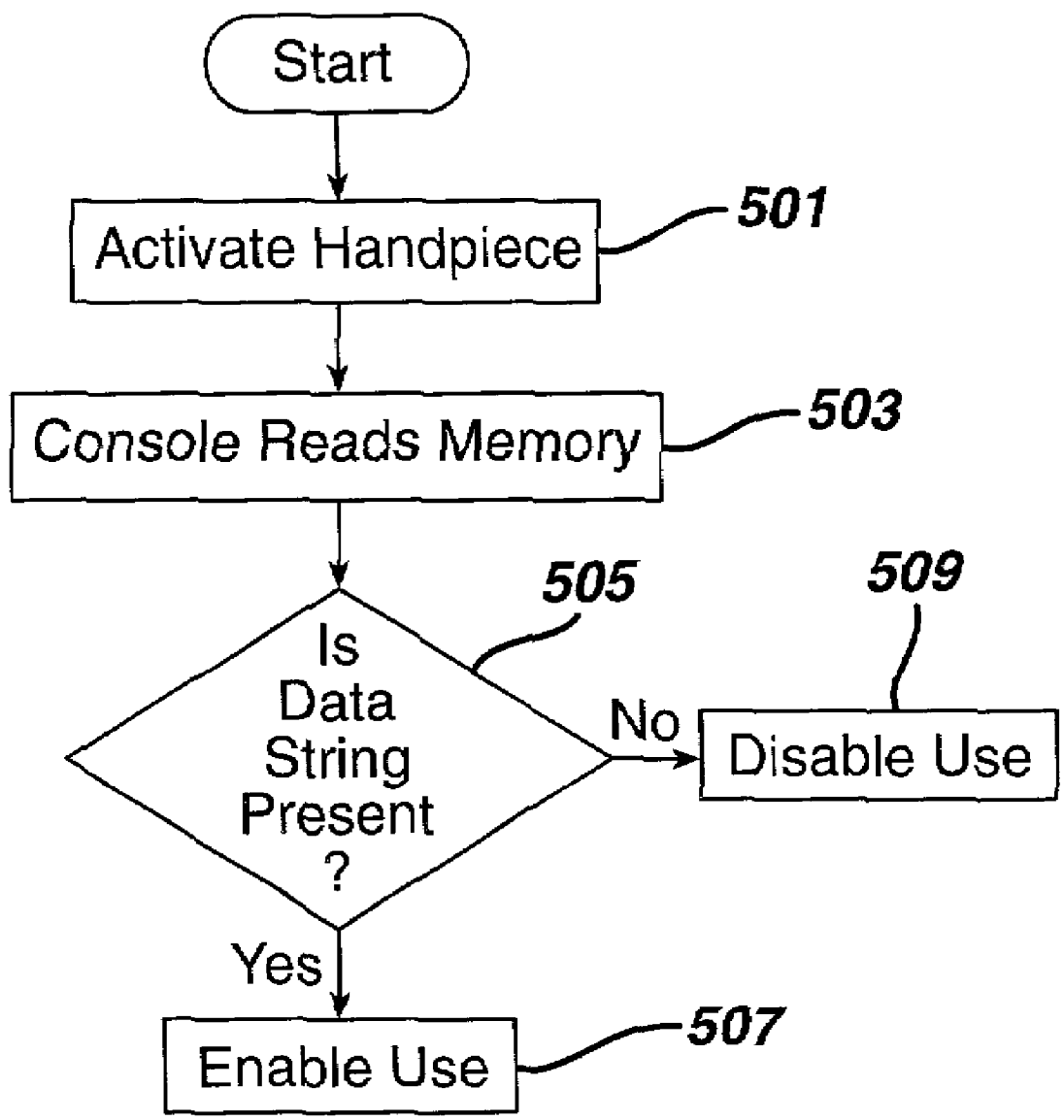
FIG. 5 is a flow diagram illustrating the operation of the non-volatile memory according to the invention as proprietary lockout for preventing inappropriate use of the ultrasonic surgical hand piece.

FIG. 5 is a flow diagram that illustrates the operation of the memory 400 as a proprietary lockout for preventing inappropriate use of the hand piece 30. The memory 400 can be utilized to prevent unauthorized, unintentional or inadvertent use of the end effector or blade or shears with the generator console 10. Inappropriate usage includes hazardous use, poor operational usage, or non-compatible use or unapproved use with the generator console 10.

Figure 5A:
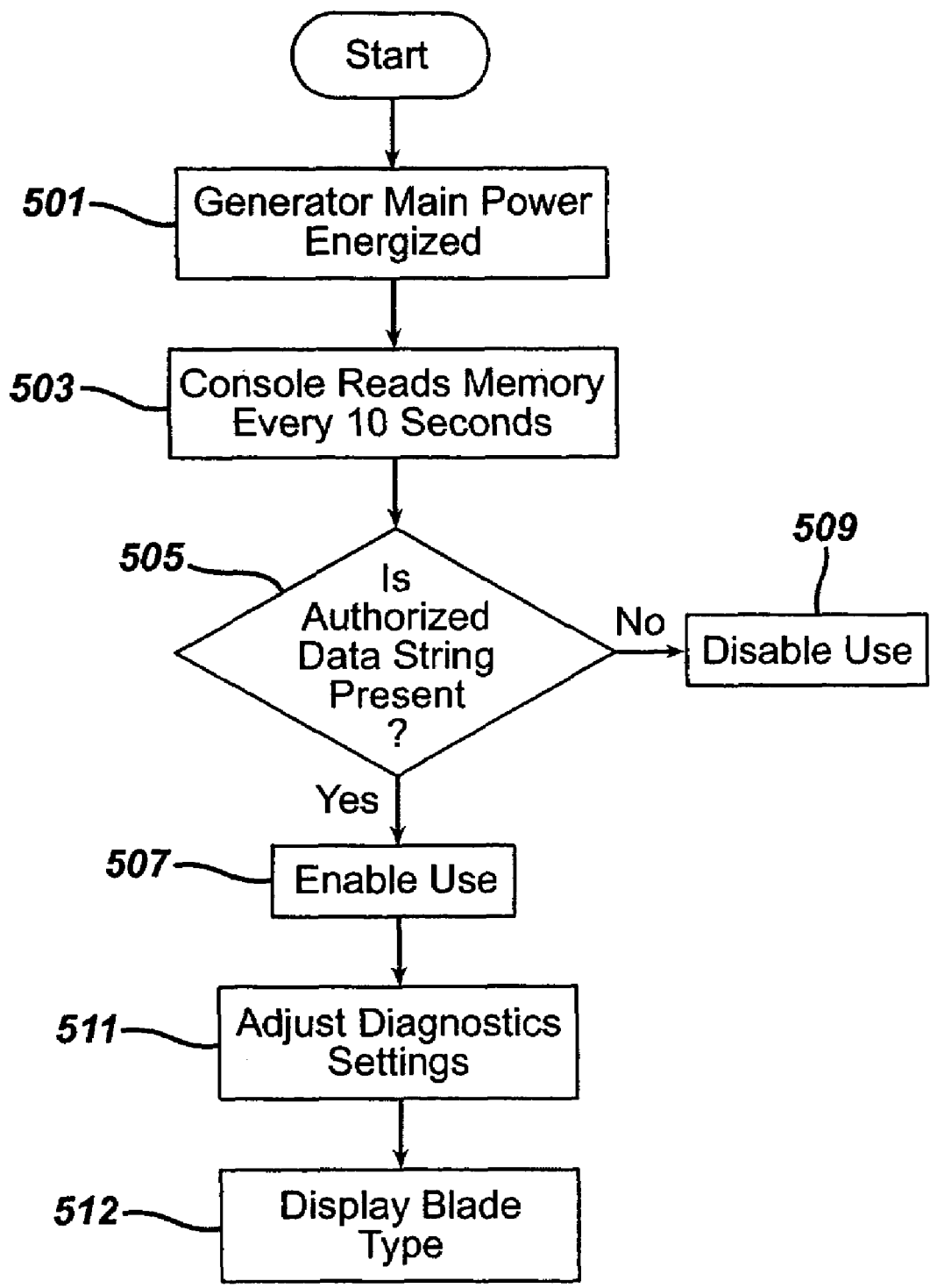
FIG. 5A is a flow diagram illustrating the operation of the non-volatile memory according to the invention.

FIG. 5A is another flow diagram that illustrates the operation of the memory 400 or 301, 302, or 303. In this particular embodiment of the method according to the invention, the memory in the blade or shears is periodically queried independent of handpiece activation, for example, at intervals of 10 seconds. This particular embodiment allows generally immediate detection of blade change and generally immediate detection of blade type attached. Such information can contribute to diagnostic functionalities that monitor handpiece temperature, temperature rate of change, and other parameters to adjust triggers and thresholds and allow the display of blade type and related parameters in the generator console in advance of the next activation.

In step 501, the handpiece 30 is activated, e.g., by pressing the button 18 on the generator console 10 for hand activation of the handpiece. In step 503, the generator console 10 then reads the memory 400. In step 505, it is determined whether a proprietary data string is present in the memory 400. The data string, input into the non-volatile memory for all authorized hand pieces, is in digital or analog form. The data string can also be a musical, speech, or sound effect in either digital or analog format. Having a proper proprietary string in the memory 400 means that the use of the hand piece with the generator console 10 is authorized or authenticated. If the data string is present in the memory 400, the hand piece 30 is enabled or activated by the generator console 10 (step 507). If the data string is not present in the memory 400 or an improper data string is present, the hand piece 30 is not enabled (step 509), and an error message appears on the display device 12 at the generator console 10 indicating unauthorized use.

In a specific embodiment according to the invention, when the generator console 10 reads the data string in the memory 400, a cyclical redundancy check (CRC) is used to detect read errors and/or to authenticate the hand piece. A CRC is a mathematical method that permits errors in long runs of data to be detected with a very high degree of accuracy. Before data is transmitted over a phone, for example, the sender can compute a 32-bit CRC value from the data's contents. If the receiver computes a different CRC value, then the data was corrupted during transmission. Matching CRC values confirms with near certainty that the data was transmitted intact.

According to the CRC authentication technique, the entire block of data is treated as a long binary number which is divided by a conveniently small number and the remainder is used as the check value that is tacked onto the end of the data block. Choosing a prime number as the divisor provides excellent error detection. The number representing the complete block (main data plus CRC value) is always a multiple of the original divisor, so using the same divisor always results in a new remainder of zero. This means that the same division process can be used to check incoming data as is used to generate the CRC value for outgoing data. At the transmitter, the remainder is (usually) non-zero and is sent immediately after the real data. At the receiver, the entire data block is checked and if the remainder is zero, then the data transmission is confirmed.

An 8-bit CRC generator can be implemented in hardware, software or firmware in the memory 400. Firmware is the controller software for a hardware device, which can be written or programmed in a non-volatile memory (e.g., memory 400) such as an EEPROM or flash ROM (read only memory). The firmware can be updated with a flash program for detection and correction of bugs in the controller software or to improve performance of the hardware device. An exemplary EEPROM used in implementing the invention is the 256-bit DS2430A 1 wire device organized as one page of 32 bytes for random access with a 64-bit one-time programmable application register, which is a part of the iButton™ family of hardware devices commercially available from Dallas Semiconductor™.

The following exemplary software code in "C" which is a commonly used programming language in the art, illustrates how the 8-bit CRC is calculated when reading the data string in the memory 400 for authenticating use of the hand piece with the generator console 10. Prior to the calculation of the CRC of a block of data, the 8-bit CRC is first initialized to zero. When the generator console 10 reads the 8 bytes of the data string in the memory 400, an 8-bit CRC is calculated for each of the 8 bytes of the data string. If the resultant 8-bit CRC is equal to zero, then the use of the hand piece with the generator console 10 is authenticated, and the hand piece is enabled. If the resultant 8-bit CRC is not equal to zero, then the use of the hand piece with the generator console 10 is not authenticated, the hand piece not enabled, and an error message appears on the display device 12 at the generator console 10 indicating unauthorized use.

```
/*
=========================================================
FUNCTION
    mlan_CRC8
PASSED PARAMETERS
    'data' - data byte to calculate the 8 bit crc from
    'crc8' - the current CRC.
RETURN
    the updated 8 bit CRC.
=========================================================
/*
static uchar crc_table[] =
{
    0, 94, 188,226, 97, 63,221, 131, 194,156,126, 32,163,253, 31, 65
    157,195, 33,127,252,162, 64, 30, 95, 1,227, 189, 62, 96,130,220,
    190,224, 2, 92,223,129, 99, 61,124, 34, 192,158, 29, 67,161,255,
    70, 24,250,164, 39,121,155,197,132,218 56,102,229,187, 89,7,
    219,133,103,57,186,228, 6, 88, 25, 71, 165,251,120, 38,196,154,
    101, 59,217,135, 4, 90,184,230,167,249, 27, 69,198,152,122,36,
    248,166, 68, 26,153,199, 37,123, 58,100,134,216, 91, 5,231,185
    140,210, 48,110,237,179, 81, 15, 78, 16,242,172, 47,113,147,205,
    17, 79,173,243,112, 46,204,146,211, 141,111, 49,178,236, 14, 80,
    175,241, 19, 77,206,144,114, 44,109, 51,209,143, 12, 82,176,238,
    50,108,142,208, 83, 13,239,177,240,174, 76, 18,145,207, 45,115,
    202,148,118, 40,171,245, 23, 73, 8, 86,180,234,105, 55,213,139,
    87, 9,235,181, 54,104,138,212,149,203, 41,119,244,170, 72, 22,
    233,183, 85, 11,136,214, 52,106, 43,117,151,201, 74, 20,246,168,
    116, 42,200,150, 21, 75,169,247,182,232, 10, 84,215,137,107,53
};
uchar mlan_CRC8(uchar data, uchar crc8)
{
    return crc_table[crc8 ^ data];
}
```

Another exemplary software code is listed below for calculating a 16-bit CRC for the memory 400. Similarly, prior to the calculation of the CRC of a block of data, the 16-bit CRC is first initialized to zero. When the generator console 10 reads the 16 bytes of the data string in the memory 400, an 16-bit CRC is calculated for each of bytes 1 through 30 of the data string, and the results are stored in bytes 31 and 32. After comparing the results, if the resultant CRC is equal to zero, then the use of the hand piece with the generator console 10 is authenticated, and the hand piece is enabled. If the resultant CRC is not equal to zero, then the use of the hand piece with the generator console 10 is not authenticated, the hand piece not enabled, and an error message appears on the display device 12 at the generator console 10 indicating unauthorized use.

```
/*
=========================================================
FUNCTION
    mlan_CRC16
PASSED PARAMETERS
    'data' - current word to add into the CRC
    'crc16' - the current value of the 16 bit CRC
RETURN
    new value of the 16 bit CRC
=========================================================
/*
static int oddparity[16] = {0, 1, 1, 0, 1, 0, 0, 1, 1, 0, 0, 1, 0, 1, 1, 0};
uint mlan-CRC16(uint data, uint crc16)
{
    data = (data ^ (crc16 & 0xff)) & 0xff;
    crc16>>=8;
if (oddparity[data & 0xf]^ oddparity[data >> 4])
    crc16 ^=0xc001;
data <<=6;
crc16 ^= data;
data <<= 1;
crc16 ^= data;
return crc16;
}
```

Furthermore, the data string in the memory 400 can be an encrypted code which, when decoded by a corresponding encryption algorithm resident at the generator console 10, provides a responding data pattern that serves to authenticate proper usage of the hand piece with the console. Encryption is achieved with algorithms that use a computer "key" to encrypt and decrypt messages by turning text or other data into an unrecognizable digital form and then by restoring it to its original form. The longer the "key," the more computing is required to crack the code. To decipher an encrypted message by brute force, one would need to try every possible key. Computer keys are made of "bits" of information of various length. For instance, an 8-bit key has 256 (2 to the eighth power) possible values. A 56-bit key creates 72 quadrillion possible combinations. If the key is 128 bits long, or the equivalent of a 16-character message on a personal computer, a brute-force attack would be 4.7 sextillion (4,700,000,000,000,000,000,000) times more difficult than cracking a 56-bit key. With encryption, unauthorized use of the hand piece with the generator console 10 is generally prevented, with a rare possibility of the encrypted code being deciphered for unauthenticated use.

A unique identification (ID) number is registered and stored in the memory (e.g., memory 400 or 301) for every hand piece and blade and shears manufactured which is compatible for use with the generator console 10, where identity is assured since no two hand pieces or blades or shears are alike. In a specific embodiment according to the invention, the memory 400 is the DS2430A 1 wire EEPROM device, commercially available from DALLAS SEMICONDUCTOR™, which stores a factory-lasered and tested 64-bit ID number for each hand piece manufactured. The ID number can be a model or model family number, in addition to being a unique serial number ID for each individual hand piece. This allows the generator console 10 to acknowledge its compatibility and useability therewith, without requiring a list of serial numbers for that model or model family. Foundry lock data in a hardware format and protocol is stored in the memory 400 to ensure compatibility with other products of generally the same communications protocol, e.g., the products of the MICROLAN™ protocol commercially available from DALLAS SEMICONDUCTOR™. This advantageously provides scalability for providing a system with additional surgical devices on a local area network (LAN) operated on generally the same communications protocol.

Once the hand piece 30 is enabled or activated by the generator console 10 (set 507), the diagnostics settings of the hand piece generator are adjusted, as indicated in step 511. Here, the system performs diagnostic tests to determine whether a reprogram or upgrade of the generator console is needed. If it is determined that a reprogram or upgrade is needed, the generator console reads the memory located in the sheath of the end-effector of the hand piece where a reprogram or upgrade code is stored. Using the reprogram or upgrade code read from the memory, the generator console is reprogrammed or upgraded accordingly. This permits automatic upgrades of the generator consoles in the "field" without having to return them to the manufacturer or to send a service technician to where the generator console is physically located.

In alternative embodiments, rather than reprogramming the generator memory, the blade/shear memory data is utilized by the generator console as the basis for setting operation parameters for the particular blade/shear in use.

Subsequent to the adjustment of the diagnostic setting, the type of blade that is connected to the hand piece is displayed on the console display 12.

Figure 6:
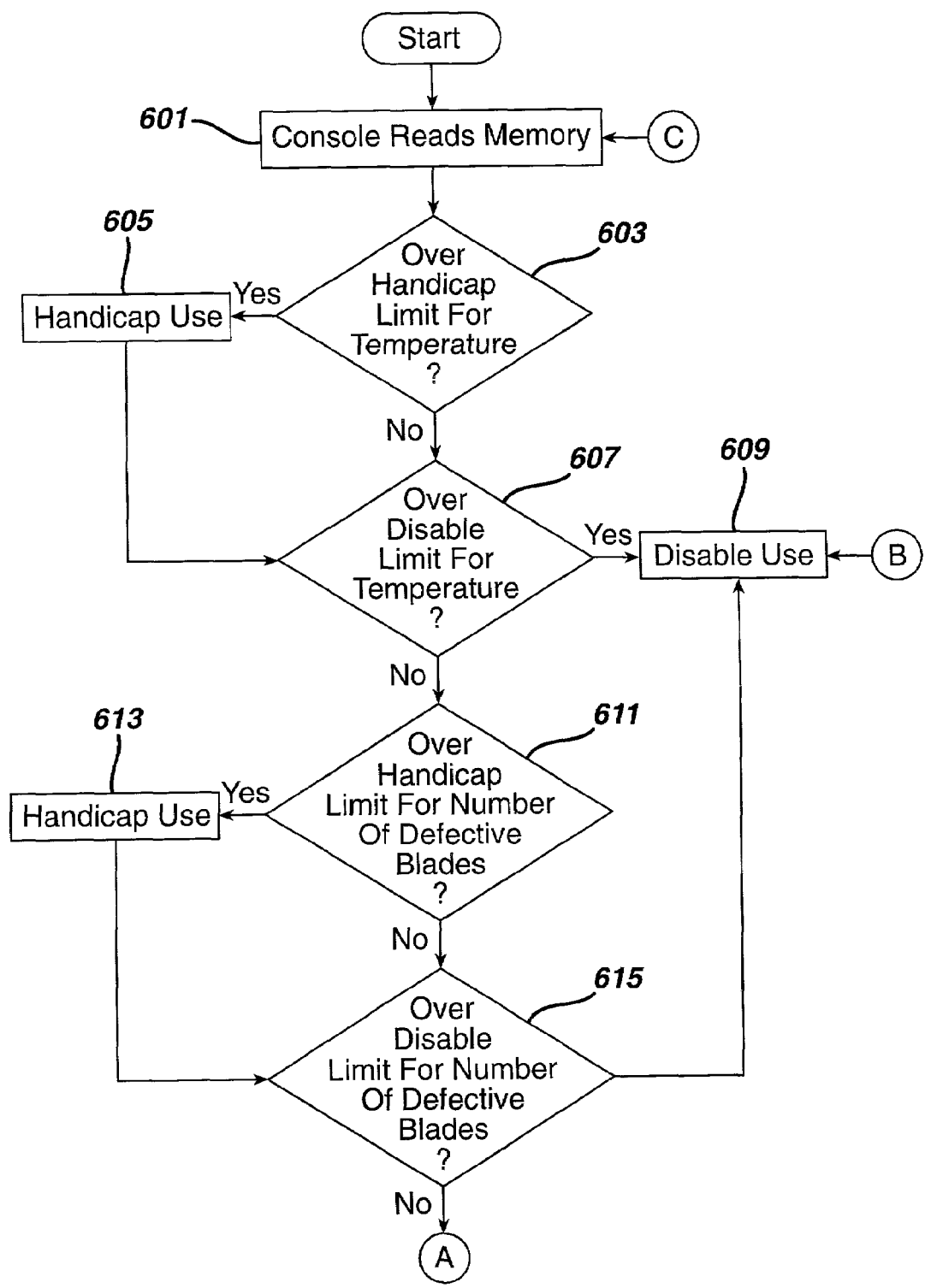
FIG. 6 and FIG. 7 are flow diagrams illustrating the operation of the non-volatile memory according to the invention for error prevention when using the ultrasonic surgical hand piece.
Figure 7:
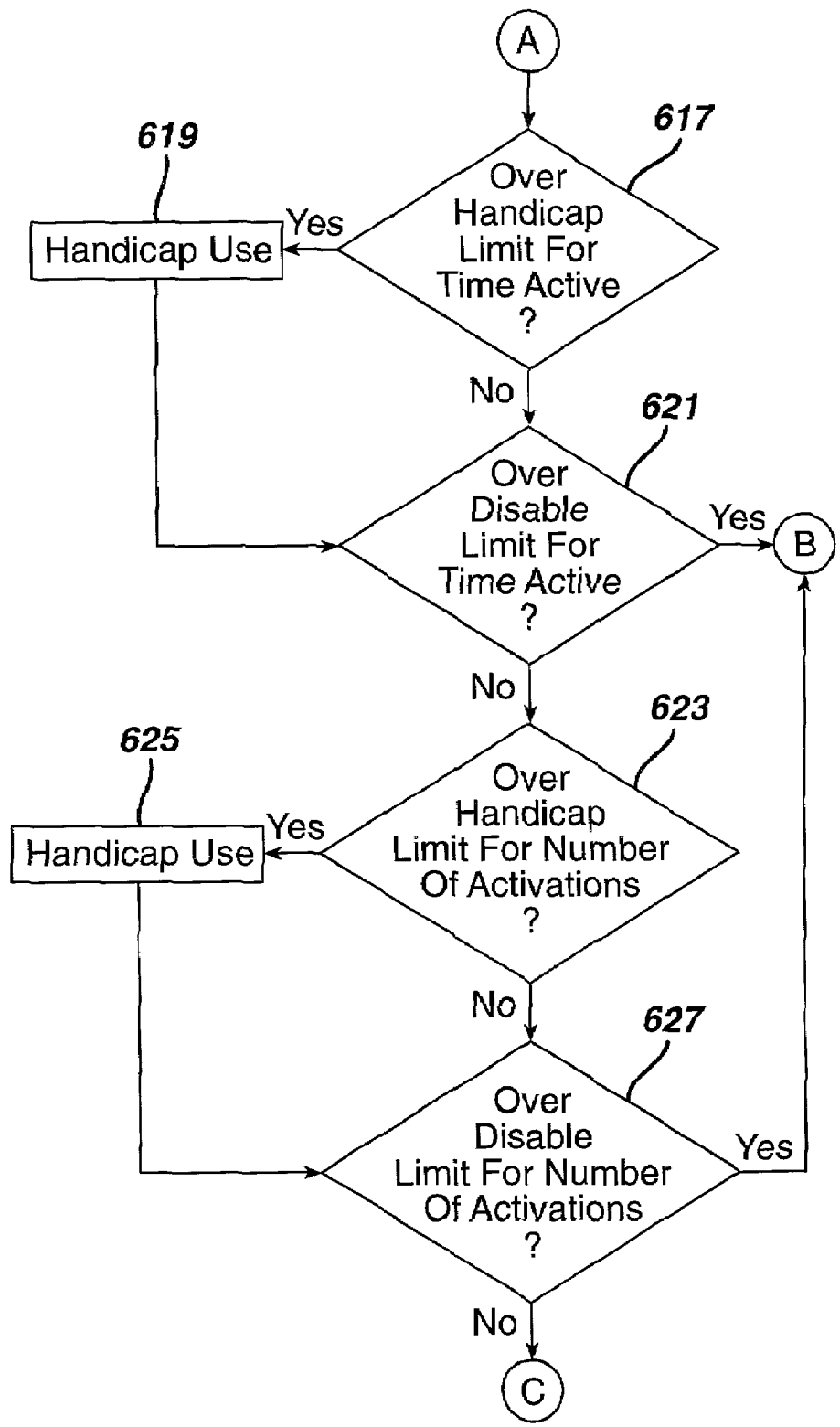

FIG. 6 and FIG. 7 are flow diagrams that illustrate the operation of the memory 400 or 301 according to the invention for error prevention when using the handpiece 30 with the generator console 10. To prevent errors in operating the handpiece 30, the memory 400 or 301 can store certain diagnostic information which the generator console 10 can utilize in determining whether the operation of the handpiece 30 should be handicapped or disabled. For instance, the memory 400 or 301 can store information such as limits on the time that the hand piece is active, the number of activations within a time period, the number of defective blades used, operating temperature, allowable temperature rate of change, and any other performance characteristics such as, e.g., those listed in Table 1. Those skilled in the art can appreciate that other error prevention, diagnostic and performance characteristics can be stored in memory 400 or 301. Exemplary performance characteristics that can be stored in memory 400 or 301 (as shown in Table 1) include surgical device type information and revision data (row 1 in Table 1), current set point (row 2), transducer capacitance (row 3), cable capacitance (row 4), phase margin for the handpiece equipped with a test tip or end-effector (row 5), resonant frequency (row 6), remaining operating procedures (row 7), lower bound or threshold on operating frequency (row 8, upper bound or threshold on operating frequency (row 9), maximum output power (row 10), power control information and authorization (row 11, handpiece impedance (row 12), total on-time information at specific power levels (rows 13 and 14), handpiece enable/disable diagnostics information (row 15), handpiece error codes (row 16), temperature range and change data (rows 17, 18 and 19), current excess load limit (row 20), high impedance fault limit (row 21), and cyclical redundancy check (CRC) data (row 22). Other characteristics such as blade dampening behavior can also be stored in the memory.

Moreover, the memory 400 can store user-specific data such as user name, internal tracking number, calibration schedule, and custom output performance specifications. The user-specific data can be manipulated or programmed through the generator console 10 or initialized at the time the end effector is made at the factory. In addition, the memory can be used in conjunction of specialized instruments such as cartery or self-heating devices, homogenizers and liquifiers.

TABLE 1

| | |
|---|---|
| 1 | Bits 1-3: Device Type |
| | Bits 4-8: Revision |
| 2 | Current set point |
| | $I_{setpoint}$ |
| 3 | Transducer Capacitance |
| | $C_o$ |
| 4 | Cable Capacitance |
| | $C_c$ |
| 5 | Phase margin with test tip |
| | $Pm_0$ |
| 6 | Resonance frequency |
| | $f_{ro}$ |
| 7 | Allowed Procedures Remaining |
| 8 | Lower bound on seek/lock frequency |
| | (offset from $f_{ro}$) |
| | $f_{lower\ bound}$ |
| 9 | Upper bound on seek/lock frequency |
| | (offset from $f_{ro}$) |
| | $f_{upper\ bound}$ |
| 10 | Maximum output power @ level 5 $W_{max}$. |

TABLE 1-continued

| | |
|---|---|
| 11 | Bit 1 Backside power curve control variable:<br>Capped Power = 1; Descending power = 0<br>Bit 2; Single cap at all levels = 1,<br>Different cap for each power level = 0<br>Bit 3: Hand piece Authorized Activation Flag.<br>Bits 4-8: Unused |
| 12 | Hand piece Impedance, Re \|Z\| |
| 13 | Total On-Time @ level 5 |
| 14 | Total on-Time @ level <5 |
| 15 | Hand piece Diagnostics Enable/Disable Flags byte no. 1<br>Hand piece Diagnostics Enable/Disable Flags byte no. 2 |
| 16 | Hand piece error code 1 (newest)<br>Hand piece error code 2<br>Hand piece error code 3<br>Hand piece error code 4<br>Hand piece error code 5 (oldest) |
| 17 | $\Delta C_o$ Over Temp Entry |
| 18 | $\Delta C_o$ Over Temp Exit |
| 19 | $C_o$ Max Rate of Change |
| 20 | Current Excessive Load Limit |
| 21 | High Impedance with test tip fault limit |
| 22 | Data CRC |

Figure 6A:
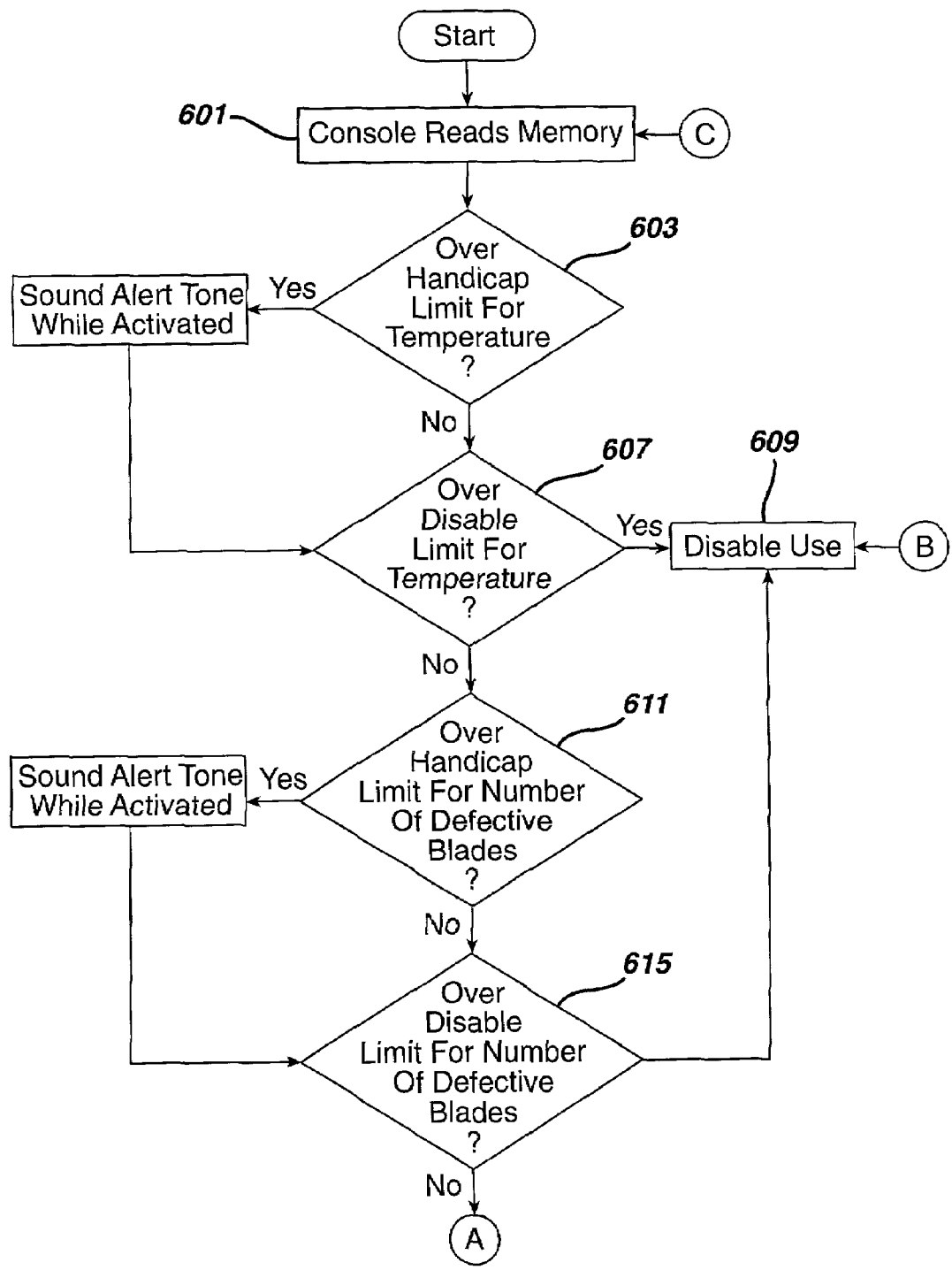
FIG. 6A and FIG. 7A are flow diagrams illustrating the operation of the non-volatile memory according to the invention.
Figure 7A:
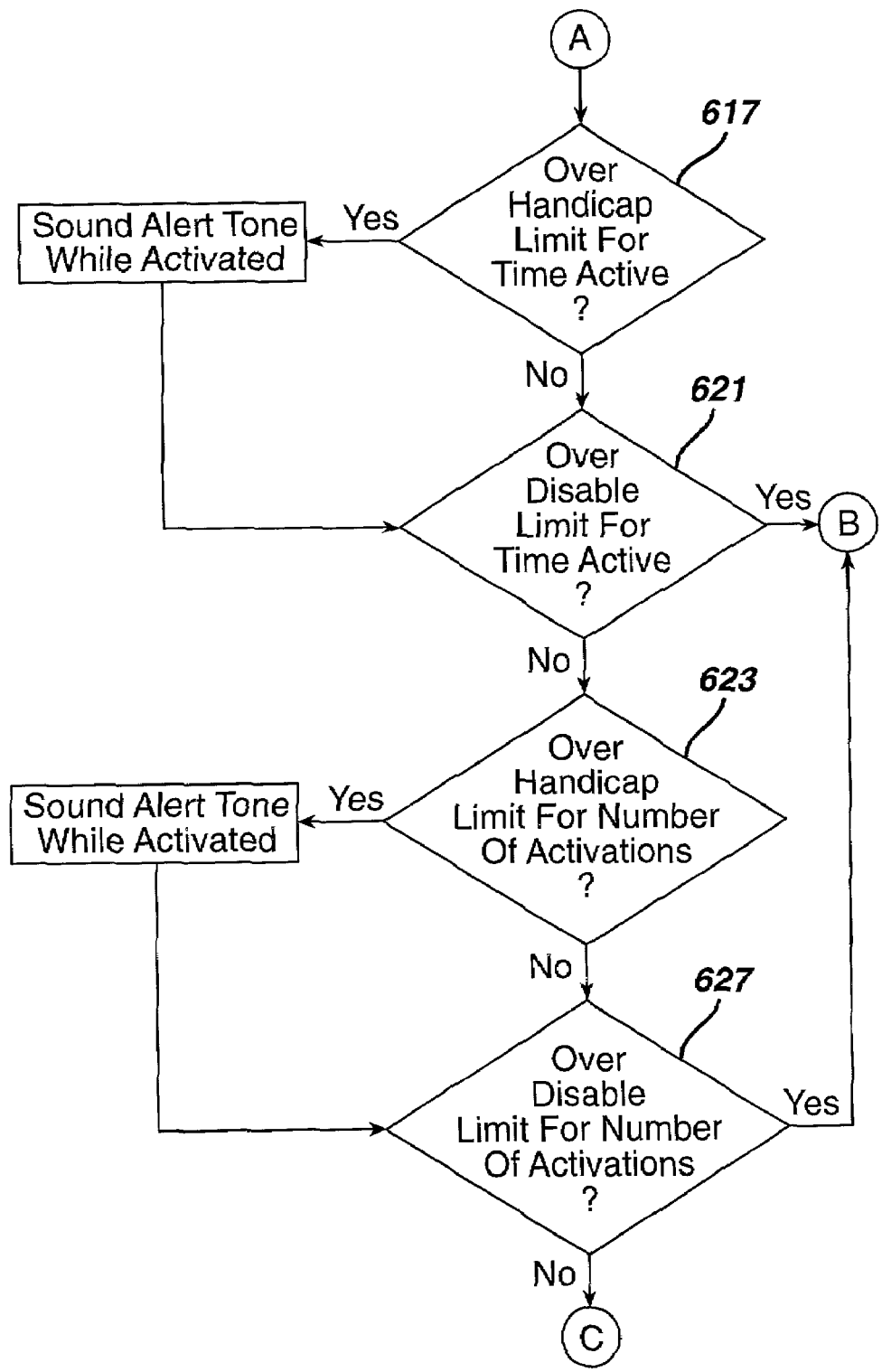

FIG. 6A and FIG. 7A are flow diagrams that illustrate the alerting of an end user to issues or difficulties triggered by parameters stored in the blade/shears memory. Rather than handicapping or reducing functional capabilities, which can interrupt or degrade the surgeon's ability to perform the procedure, this particular embodiment of the method according to the invention allows the end user to manually halt use at a convenient point in context with the nature of the alarm and the surgical work immediately at hand.

According to a specific embodiment of the invention, once the handpiece 30 is activated for use, the generator console 10 reads the memory 400 or 301 (step 601) for the diagnostic information. In step 603, the generator console 10 determines whether the temperature of the handpiece 30 is over the handicap limit stored in the memory 400. If so, the generator console 10 then instructs the handpiece 30 to operate in the handicap mode (step 605), e.g., operating below a certain speed or vibrational frequency or in a limited mode such as coagulation or cutting in order to avoid overheating. If not, the flow control goes to step 607, where the generator console 10 determines whether the temperature of the handpiece 30 is over the disable limit stored in the memory 400. If so, the generator console 10 disables the handpiece 30 (step 609). If not, the flow control goes to step 611, where the generator console 10 determines whether the number of defective blades found within a time period of operating the handpiece 30 has exceeded the handicap limit stored in the memory 400. If so, the generator console 10 then instructs the hand piece 30 to operate in the handicap mode (step 613), e.g., operating below a certain speed or vibrational frequency or in a limited mode such as coagulation or cutting in order to decrease the incidence of causing the blade 32 to become defective. The handicap mode in step 613 is not necessarily the same as the handicap mode in step 605, depending on the optimal mode for operating the handpiece 30 under the circumstances with respect to steps 603 and 611.

If the number of defective blades found has not exceeded the handicap limit, the flow control is directed to step 615, where the generator console 10 determines whether the number of defective blades found within a time period has exceeded the disable limit stored in the memory 400. If so, the generator console 10 disables the handpiece 30 (step 609). If not, the control flow is directed, via step A, to step 617, where the generator console 10 determines whether the time the handpiece 30 has been active has exceeded the handicap limit stored in memory 400. If so, the generator console 10 instructs the handpiece 30 to operate in a handicap mode, e.g., operating below a certain speed or vibrational frequency or in a limited mode such as coagulation or cutting. The handicap mode in step 619 is not necessarily the same as the handicap mode in steps 605 or 613, depending on the optimal mode for operating the handpiece 30 under the circumstances with respect to steps 603, 611 and 617.

If the time the handpiece 30 has been active has not exceeded the handicap limit, the flow control is directed to step 621, where the generator console 10 determines whether the time the hand piece has been active has exceeded the disable limit stored in the memory 400. If so, the control flow is directed, via step B, to step 609 where the generator console 10 disables the handpiece 30. If not, the control flow goes to step 623, where the generator console 10 determines whether the number of activations for the handpiece 30 within a time period has exceeded the handicap limit stored in memory 400. If so, the generator console 10 instructs the handpiece 30 to operate in a handicap mode (step 625), e.g., operating below a certain speed or vibrational frequency or in a limited mode such as coagulation or cutting. The handicap mode in step 625 is not necessarily the same as the handicap mode in steps 605, 613 or 619, depending on the optimal mode for operating the handpiece 30 under the circumstances with respect to steps 603, 611, 617 and 623.

If the number of activations for the handpiece 30 within a time period has not exceeded the handicap limit, the flow control is directed to step 627, where the generator console 10 determines whether the number of activations for the handpiece 30 within a time period has exceeded the disable limit stored in the memory 400. If so, the control flow is directed, via step B, to step 609 where the generator console 10 disables the handpiece 30. If not, the control flow is directed, via step C, to step 601 from which the process step according to this particular embodiment of the invention are repeated until the handpiece 30 is caused to be disabled.

The disable limits and the handicap limits described herein with respect to FIG. 6 and FIG. 7 may be of substantively different criteria for the generator console 10 to determine the operational mode of the handpiece 30. The memory 400 may be re-initialized for different disable or handicap limits for varied operational conditions of the handpiece 30. The generator console 10 may likewise be re-initialized to operate on varied criteria for controlling the operational mode of the handpiece 30 based on the information stored in the memory 400.

Figure 8:
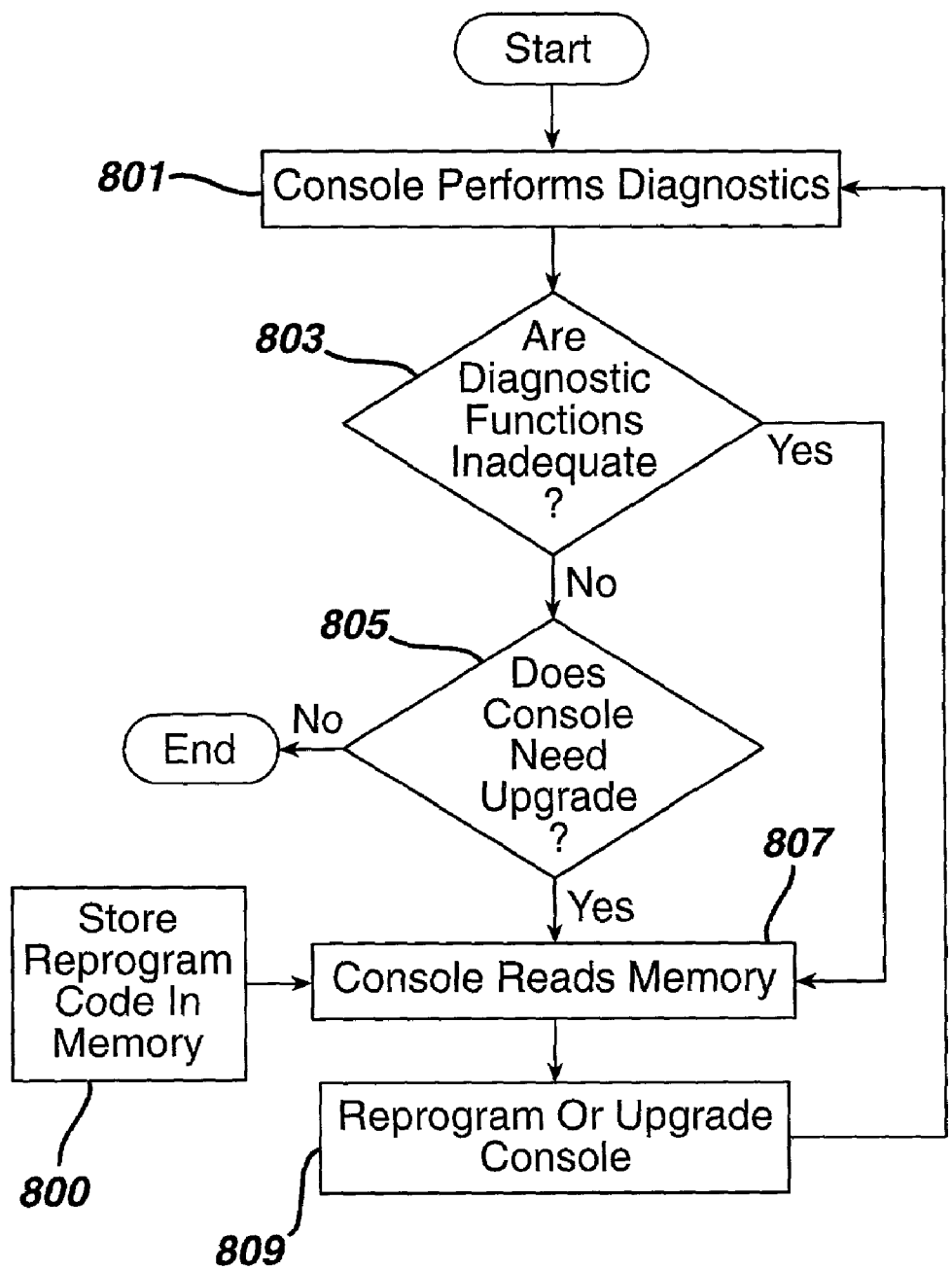
FIG. 8 is a flow diagram illustrating the operation of the non-volatile memory according to the invention for reprogramming or upgrading the console using the hand piece.

FIG. 8 is a flow diagram that illustrates the operation of the memory 400 according to the invention for reprogramming or upgrading the generator console 10 using the handpiece 30. In step 801, the generator console 10 performs diagnostic tests on the functions of the console. It is determined in step 803 whether any functions are deemed inadequate, e.g., functions that need to be altered, disabled or added. For example, the error prevention functions described herein with respect to FIG. 6 and FIG. 7 may need to be added, or the handicap limits and operational modes may need to be re-initialized. If it is determined that certain functions are inadequate, the flow control is directed to step 807. In step 807, the generator console 10 reads the memory 400 of the handpiece 30 where the reprogram code has been stored in step 800. Using the reprogram code read from the memory 400, the functions of the generator console 10 is reprogrammed.

If it is determined in step 803 that the functions of the generator console 10 are adequate or the memory has a newer version of the program, then the generator console 10 has the flow control directed to step 805. It is determined in step 805 whether an upgrade is needed for the generator console 10. If so, the flow control is directed to step 807. In step 807, the generator console 10 reads the memory 400 of the handpiece 30 where the reprogram or upgrade code has been stored in step 800. Using the reprogram or upgrade code read from the memory 400, the functions of the generator console 10 is reprogrammed and upgraded. For example, if the generator console 10 is experiencing operational difficulties with a specific generation or version of the hand piece, an upgrade from the memory 400 instructs the generator console 10 to allow its use with only newer versions or generations of the hand piece. The memory 400 can also store information including the manufacture date, design revision, manufacturing code, lot code or other manufacture-related information for a specific grouping of hand pieces according to generation or version having operational difficulties or defectiveness, from which the generator console 10 can be reprogrammed or upgraded to refuse activation for use with such hand pieces.

In addition to storing reprogram or upgrade code, the memory 400 can also store performance criteria for operating the handpiece 30 with the generator console 10. For example, the memory 400 can store energy level information such as a maximum energy level for driving the particular handpiece 30, because, e.g., a relatively small hand piece may not be able to be driven, in terms of energy levels, as intensely as a relatively large hand piece for large-scale surgical procedures. Information correlating the energy levels for driving the handpiece 30 and the corresponding output displacement can also be stored in the memory 400. The generator console 10 reads the energy level information stored in the memory 400 and drives the handpiece 30 according to the corresponding output displacement. In addition to energy level information, driving signal characteristics, such as types of amplitude modulation, can be stored in the memory 400. Using the information stored in the memory 400, the generator console 10 and the handpiece 30 can perform the error prevention described herein with respect to FIG. 6 and FIG. 7, and the reprogramming or upgrade of the generator console 10 described herein with respect to FIG. 8.

As described herein with respect to FIG. 2 and FIG. 3 and in the related U.S. application Ser. No. 09/693,621 and incorporated herein by reference, the parts of the handpiece 30 in operational mode are designed, as a whole, to oscillate at generally the same resonant frequency, where the elements of the handpiece 30 are tuned so that the resulting length of each such element is one-half wavelength. Microprocessor or DSP 60, using a phase correction algorithm, controls the frequency at which the parts of the handpiece 30 oscillate. Upon activation of the handpiece 30, the oscillating frequency is set at a startup value or nominal resonant frequency such as 50 kHz which is stored in the memory 400 of the handpiece 30. A sweep of a frequency range between a start sweep point and a stop sweep point, whose values are also stored in the memory 400, is effected under the control of the DSP 60 until the detection of a change in impedance which indicates the approach to the resonant frequency. The change in impedance refers to the impedance of, e.g., a parallel equivalent circuit for mathematically modeling the algorithm for controlling the operation of the handpiece 30 as described in the related U.S. application Ser. No. 09/693, 621. Having obtained the resonant frequency, the parts of the handpiece 30 are caused to oscillate at that frequency.

Figure 9:
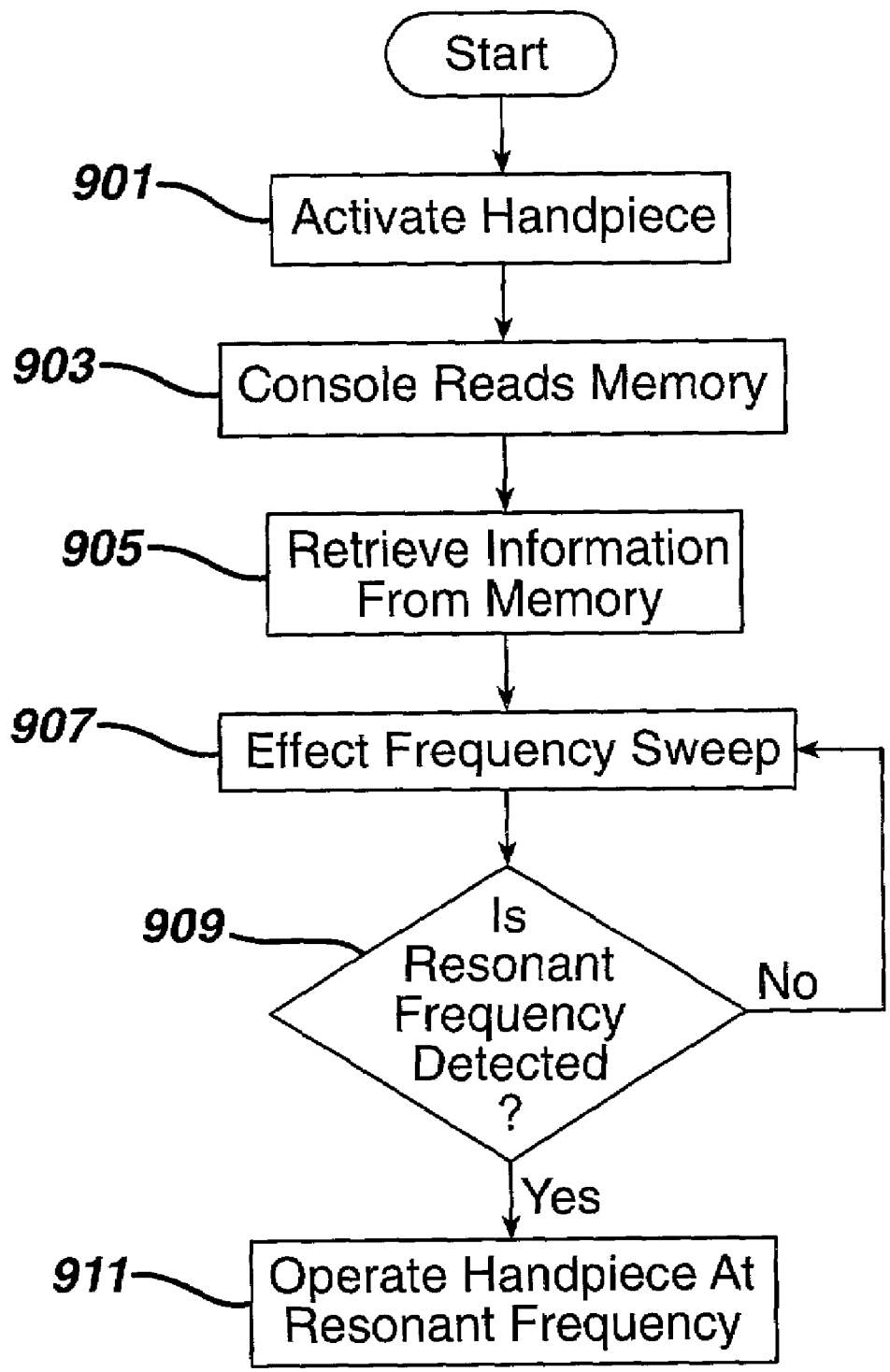
FIG. 9 is a flow diagram illustrating the operation of the ultrasonic surgical hand piece at a resonant frequency using information stored in the memory according to the invention.

FIG. 9 is a flow diagram that illustrates the operation of the handpiece 30 according to the invention at a resonant frequency using information stored in the memory 400. Once the handpiece 30 is activated (step 901), the generator console 10 reads the memory 400 of the handpiece 30 (step 903) and retrieves the information needed for operating the handpiece 30 at the resonant frequency, including the nominal resonant frequency, a frequency range delimited by a start sweep point and a stop sweep point (step 905). A frequency sweep in that frequency range is effected under the control of the DSP 60 (step 907). Detection of the resonant frequency is effected in step 909. If the resonant frequency has not yet been detected, the control flow reverts back to step 907 where the frequency sweep is continued. Upon detection of the resonant frequency, the control flow is directed to step 911 where the parts of the handpiece 30 are caused to oscillate at that resonant frequency.

Figure 10:
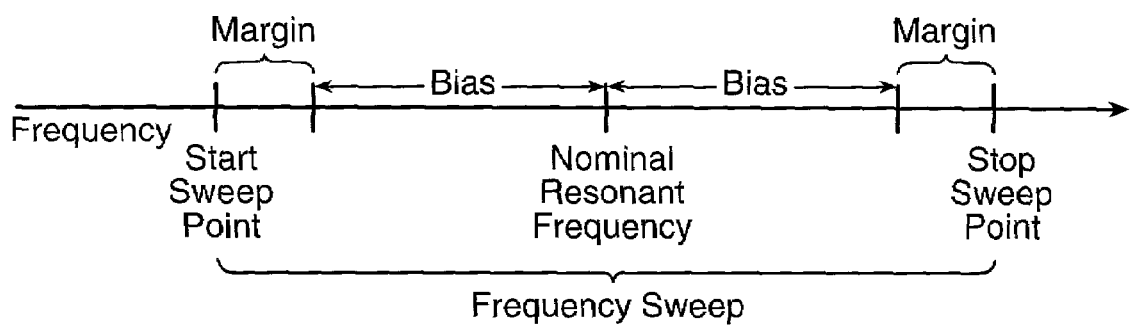
FIG. 10 is a diagram illustrating an alternative embodiment of the operation of the hand piece at a resonant frequency using information stored in the non-volatile memory according to the invention.
Figure 10A:
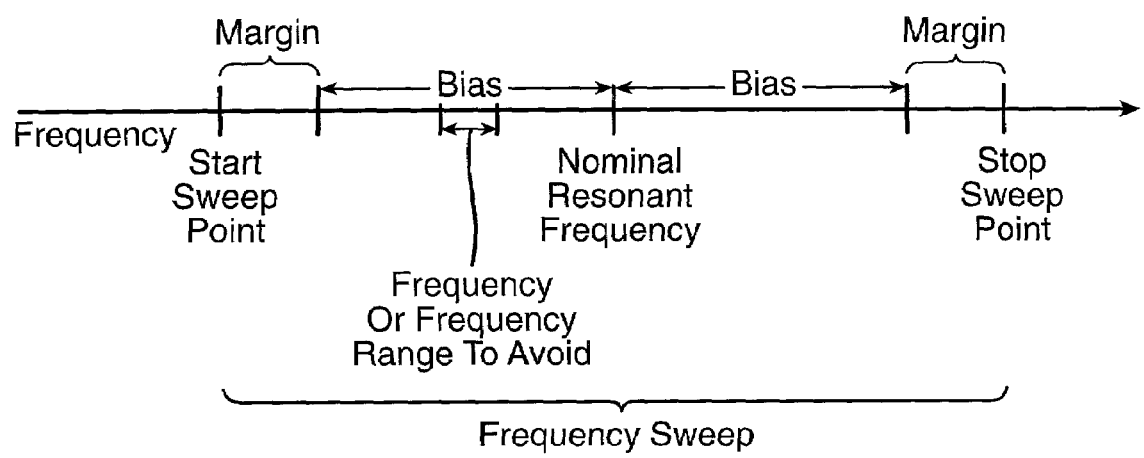
FIG. 10A is a diagram illustrating an alternative embodiment whereby frequencies to avoid operating the handpiece are included in the blade/shears memory.

FIG. 10 is a diagram that illustrates an alternative embodiment of the operation of the handpiece 30 according to the invention at a resonant frequency using information stored in the memory 400. Instead of storing the start and stop sweep points of a frequency range for the frequency sweep, the memory 400 or 301 stores the nominal resonant frequency and a bias amount. The generator console 10 calculates the start and stop sweep points by subtracting and adding the bias amount from the nominal resonant frequency, respectively. A margin, which is a relatively small amount beyond bias, is tacked on to the bias amount to respectively reach the start and stop sweep points of the frequency range in which the frequency sweep for seeking a resonant frequency is conducted. Once the resonant frequency is found, the parts of the handpiece 30 are caused to oscillate at that resonant frequency.

Using FIG. 9, the operation of the handpiece 30 according to the invention at a resonant frequency using information stored in the memory 400 or 301 is illustrated in accordance with this particular embodiment. Once the handpiece 30 is activated (step 901), the generator console 10 reads the memory 400 of the handpiece 30 (step 903) and retrieves the information needed for operating the handpiece 30 at the resonant frequency, including the nominal resonant frequency, the bias amount and the margin amount (step 905), from which a frequency range is accordingly calculated as described herein with respect to FIG. 10. The generator console 10 calculates the start and stop sweep points by subtracting and adding the bias amount from the nominal resonant frequency, respectively. The margin amount, which is a relatively small amount beyond bias, is tacked on to the bias amount to respectively reach the start and stop sweep points of the frequency range in which the frequency sweep for seeking a resonant frequency is conducted. The frequency sweep in that frequency range is effected under the control of the DSP 60 (step 907). Detection of the resonant frequency is effected in step 909. If the resonant frequency has not yet been detected, the control flow reverts back to step 907 where the frequency sweep is continued. Upon detection of the resonant frequency, the control flow is directed to step 911 where the parts of the handpiece 30 are caused to oscillate at that resonant frequency.

The memory 400 for an ultrasonic surgical handpiece 30 according to the invention is located in the sheath of the end-effector. Alternately, the memory device, 301, 302, or 303, can be located in the grip, mount, or handle portion of a shears or shears-like device or other device. The memory device 400 can also be located in one or more locations, including the electrical connector, within the housing of the handpiece 30, or at an in-line location in the cable 20. In addition to being an EEPROM, the memory 400 be one or a combination of a Read Only Memory (ROM), Erasable Programmable Read Only Memory (EPROM), Random Access Memory (RAM) or any other volatile memory which is powered by a cell, battery, or capacitor such as a super capacitor. The memory 400 can also be a Programmable Array Logic (PAL), Programmable Logic Array (PLA), analog serial storage device, sound storage integrated circuit or similar device, or a memory device in conjunction with a numeric manipulation device such as a microprocessor for the purpose of encryption. Furthermore, the memory 400 can be disposed in a non-hand piece device which can be plugged into the handpiece 30 in substitution of the end-effector.

Figure 14:
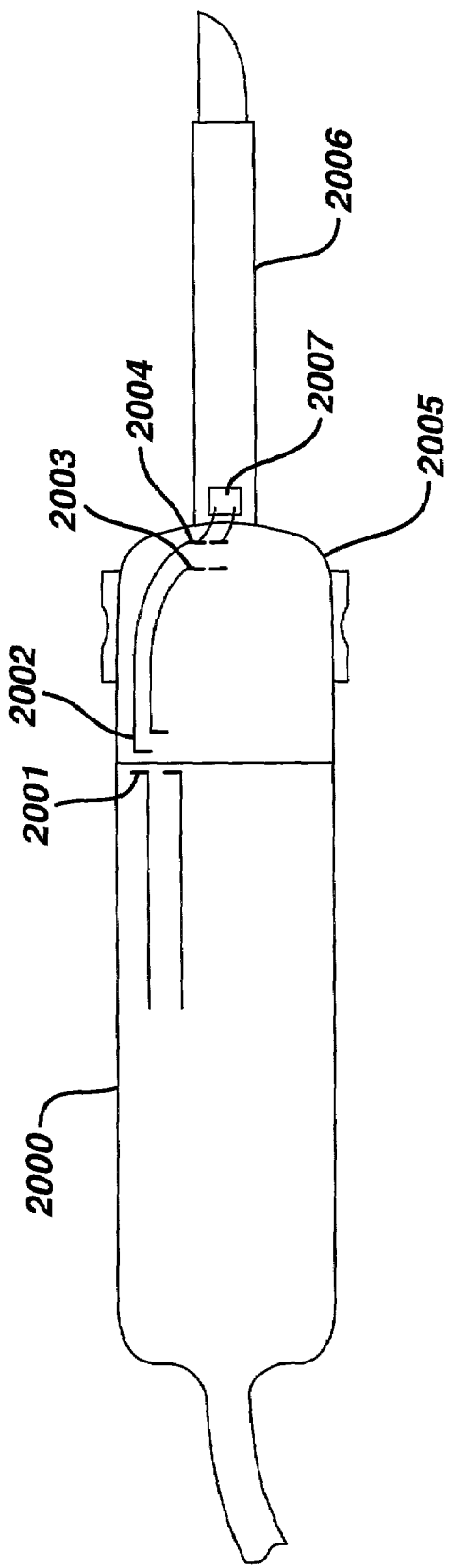
FIG. 14 is a diagram illustrating an alternative embodiment utilizing a handpiece adaptor to bridge the non-volatile memory signal to the handpiece according to the invention.

In yet another embodiment, the blade or shears or end-effector communicates electrically with the switch adaptor or adaptor rather than directly with the Handpiece. The switch adaptor conveys the signal directly or through intermediate processing to the handpiece, acting as a bridge. An example is shown in FIG. 14 where switch adaptor 2005 has contact means to the handpiece 2000 and to the blade memory contacts 2004. This construction is particularly helpful when the adaptor is a switch adaptor and there is insufficient room for passage of wiring from the blade memory directly to the handpiece itself.

Figure 15:
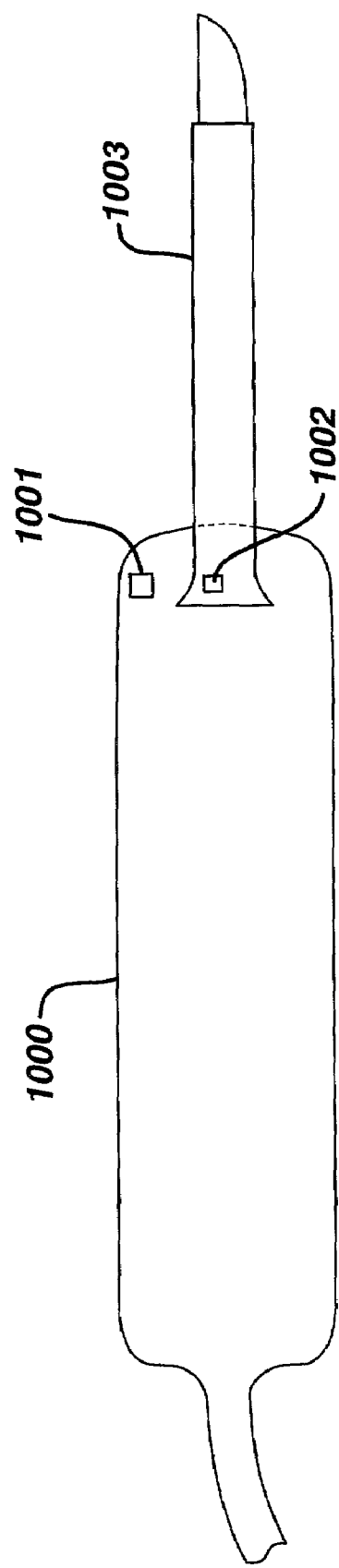
FIG. 15 is an illustration of an electromagnetic coupling means for conveying memory data to and/or from the non-volatile memory according to the invention.

In another embodiment, the memory communicates with the handpiece or with the adaptor via electromagnetic coupling instead of a direct electrical connection. In this method, the memory and support electronics is connected to a coil, all of which is mounted in or on the blade or shears or end-effector. An example is shown in FIG. 15, where a coil 1001 is located in the handpiece or the switch adaptor or the adaptor that is positioned in relatively close proximity to the memory coil 1002 located on or in the blade or shears. A circuit in the generator console drives and reads the coil 1001. Thereby, the memory is read and/or written to by the generator console without the use of direct wire connections. This method is advantageous over direct electrical contacts since it reduces complexity of end-effector fabrication. It also allows for reading and/or writing to memory of blades or shears or other end-effectors that are packaged in sterile packages which cannot be conveniently opened—yet the data in that memory needs to be known, such as number of uses previously encountered or to permit software upgrades in without opening the sterile package.

Figure 12:
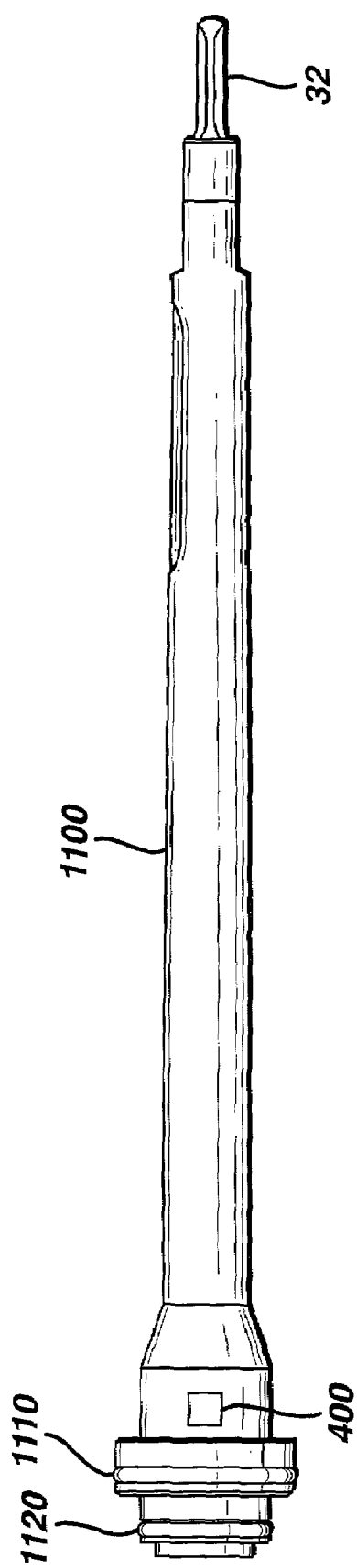
FIG. 12 is a side view of a portion of the ultrasonic surgical hand piece with a non-volatile memory in the end-effector in accordance with the invention.
Figure 13:
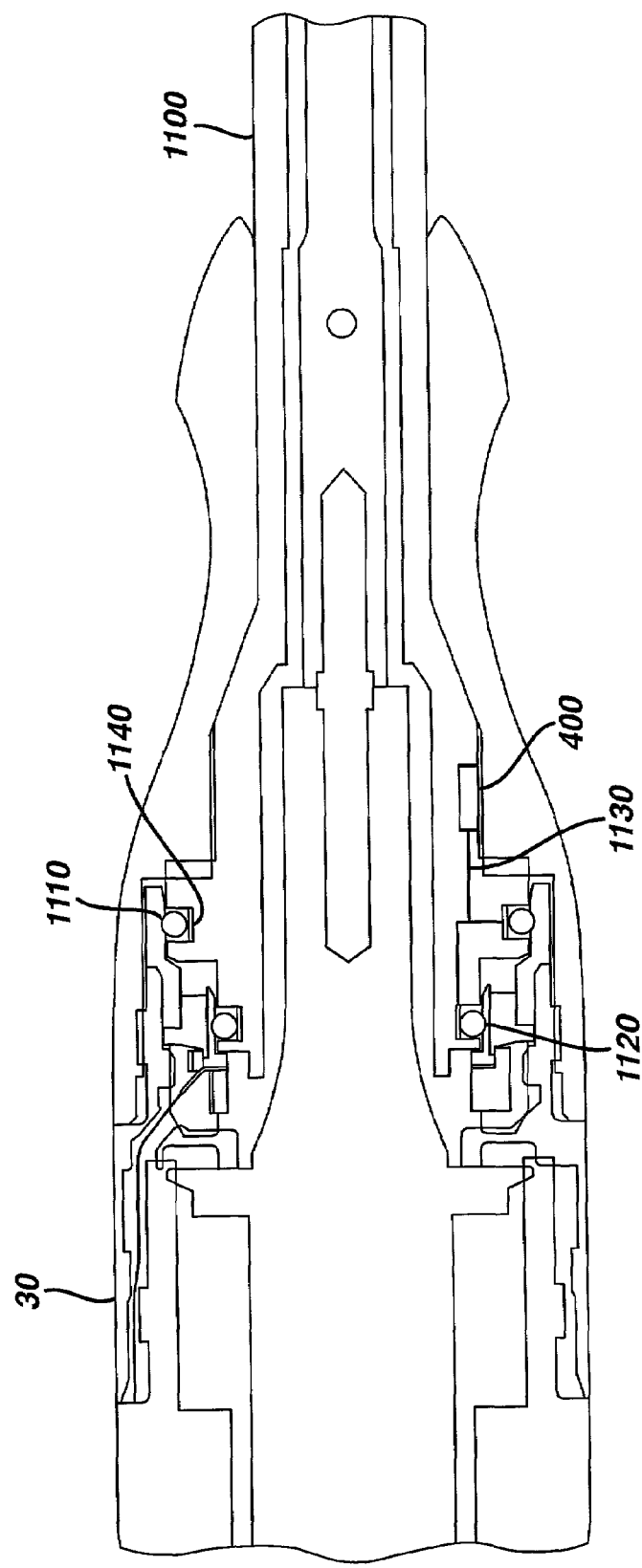
FIG. 13 is a side section view of a portion of the ultrasonic surgical hand piece with a non-volatile memory in the end-effector in accordance with the invention.

FIGS. 11, 12 and 13, respectively using an isometric view, side view and side section view, illustrate a particular embodiment of the ultrasonic surgical hand piece with a non-volatile memory (such as an EEPROM) in the end-effector in accordance with the invention.

The EEPROM 400 is embedded within the plastic handpiece 30 or housing of the ultrasonic blade 32. The EEPROM 400 has two terminations with the power/data contact 1120 and the ground contact 1110. The EEPROM 400 is embedded within the handpiece 30 using an insert or second-shot molding process. The EEPROM 400 is mounted or positioned so that the ground contact 1110, which is in contact with the blade 32, can close the circuit with the transducer 36 (FIG. 4). The other termination via the power/data contact 1120 is molded into a position that allows wire communication of power or data from the handpiece 30 to the EEPROM 400.

Referring to FIG. 13 in particular, included with the ground contact 1110 is a metal shim 1140 that is wired to the EEPROM 400. The ground contact 1110, by manipulating the metal shim 1140, can close the circuit with the external contact of the blade 32, which is isolated from the transducer 36. Also included with the power/data contact 1120 is an EEPROM wire 1130 connecting the EEPROM 400 to the contact 1120. The contact between the EEPROM 40 and the handpiece 30 can be a momentary one that is long enough for determining and authenticating the identification of the blade 32.

Although the invention has been particularly shown and described in detail with reference to the preferred embodiments thereof, the embodiments are not intended to be exhaustive or to limit the invention to the precise forms disclosed herein. It will be understood by those skilled in the art that many modifications in form and detail may be made without departing from the spirit and scope of the invention. Similarly, any process steps described herein may be interchangeable with other steps to achieve substantially the same result. All such modifications are intended to be encompassed within the scope of the invention, which is defined by the following claims and their equivalents.

We claim:

1. A system for implementing surgical procedures comprising:
   an ultrasonic surgical hand piece;
   an end-effector, said end-effector being connectable to said hand piece, and said end-effector being selected from the group consisting of a blade, an assembly of a blade and a sheath, shears, scissors and forceps;
   a generator console for controlling the hand piece, wherein the console sends a drive current to drive the hand piece, which drive current imparts ultrasonic longitudinal movement to the end-effector; and
   a memory disposed in the end-effector which adjusts operation of the generator console for operation with the end effector to set a cutting rate and degree of tissue hemostasis with the end effector, and further stores a handicap limit and a disable limit, wherein
   the console reads information stored in the memory to determine whether a copyrighted data string is present and instructs the hand piece to operate in a handicap mode if a number of defective blades found in a time period of operating the hand piece exceeds the handicap limit, and the console disables the hand piece if the number of defective blades found in the time period exceeds the disable limit;
   wherein the hand piece is authenticated for use with the console if the data string is present.

2. The system of claim 1 wherein the memory stores an alarm limit, and wherein the console instructs the hand piece to operate in an alarm mode if a temperature of the hand piece exceeds the alarm limit, and the console disables the hand piece if the temperature of the hand piece exceeds the disable limit.

3. The system of claim 1 wherein the hand piece is authenticated for use with the console using cyclical redundancy check (CRC) implemented in a firmware programmed in the memory.

4. The system of claim 1 wherein the data string is an encrypted code, and the hand piece is authenticated for use with the console by decoding the encrypted code with a corresponding encryption algorithm in the console and providing a responding data pattern.

5. The system of claim 1 wherein the console instructs the hand piece to operate in a handicap mode if a temperature of the hand piece exceeds the handicap limit, and the console disables the hand piece if the temperature of the hand piece exceeds the disable limit.

6. The system of claim 5 wherein the handicap limit and the disable limit are re-initialized based on varied operational conditions of the hand piece.

7. The system of claim 1 wherein the console instructs the hand piece to operate in a handicap mode if a time during which the hand piece has been active exceeds the handicap limit, and the console disables the hand piece if the time during which the hand piece has been active exceeds the disable limit.

8. The system of claim 1 wherein the console instructs the hand piece to operate in a handicap mode if a number of activations for the hand piece within a time period exceeds the handicap limit, and the console disables the hand piece if the number of activations for the hand piece within the time period exceeds the disable limit.

9. The system of claim 1 wherein the console is reprogrammed by reading a reprogram code stored in the memory if it is determined that a reprogram of the console is needed, and the console is upgraded by reading an upgrade code stored in the memory if it is determined that an upgrade of the console is needed.

10. The system of claim 9 wherein the console reads the reprogram code and the upgrade code from a non-volatile memory of a non-hand piece device which is plugged into the hand piece in substitution of the end-effector.

11. The system of claim 1 wherein the information stored in the memory correlates energy level information and corresponding output displacement, wherein the console reads the energy level information and drives the hand piece according to the corresponding output displacement.

12. The system of claim 1 wherein the information stored in the memory includes a nominal resonant frequency, a start sweep point and a stop sweep point delimiting a frequency range, wherein a frequency sweep in effect under control of the console is in the frequency range for detecting a resonant frequency for operating the hand piece.

13. The system of claim 1 wherein the information stored in the memory includes a nominal resonant frequency, a bias amount and a margin amount from which a frequency range is calculated, wherein a frequency sweep in effect under control of the console is in the frequency range for detecting a resonant frequency for operating the hand piece.

14. The system of claim 1 wherein the memory consists of an Electrically Erasable Programmable Read Only Memory (EEPROM), Read Only Memory (ROM), Erasable Programmable Read Only Memory (EPROM), Random Access Memory (RAM), Programmable Array Logic (PAL), Programmable Logic Array (PLA), analog serial storage device, sound storage integrated circuit, a memory device in conjunction with a numeric manipulation device including a microprocessor for the purpose of encryption, volatile memory which is powered by a device consisting of a cell, battery and capacitor.

15. A system for implementing surgical procedures comprising:
   an ultrasonic surgical handpiece;
   an end-effector connectable to said handpiece and selected from the group consisting of a blade and shears;
   a generator console having a digital signal processor for controlling the handpiece, wherein the console sends a drive current to drive the handpiece, which drive current imparts ultrasonic longitudinal movement to the end-effector;
   a memory disposed within the end-effector which adjusts operation of the generator console for operation with the end-effector to set a cutting rate and degree of tissue hemostasis with the end-effector,
   an adaptor
      wherein the memory communicates electrically with the adaptor through electromagnetic signal coupling; and
      wherein the adaptor conveys the information via the electromagnetic signal coupling to the handpiece; and
   wherein the console reads information stored in the memory and displays the information and an interpretation of the information on the console display.

16. The system of claim 15 wherein the adaptor is a switch adaptor.

17. The system of claim 15 wherein the memory is used in conjunction with specialized instruments selected from the group consisting of artery devices, homogenizers and liquifiers.

18. The system of claim 15 wherein the memory is used to determine compatibility with specific types of the handpiece and to block use of the handpiece if incompatibility with the hand piece is determined.

19. A method for implementing surgical procedures in a system including an ultrasonic surgical hand piece connectable to an end-effector, said end-effector being selected from the group consisting of a blade, an assembly of a blade and a sheath, shears, scissors and forceps, a console for controlling the hand piece, and a memory disposed in the end-effector which adjusts operation of the generator console for operation with the end-effector to set a cutting rate and degree of hemostasis with the end-effector, the method comprising the steps of:
   reading information stored in the memory;
   determining whether a copyrighted data string is present in the memory;
   authenticating use of the hand piece with the console if the data string is present;
   sending a drive current to drive the hand piece;
   imparting ultrasonic movement to the end-effector;
   periodically querying the memory during the ultrasonic movement of the end-effector to adjust operation of the console;
   instructing the hand piece to operate in a handicap mode if a number of defective blades found in a time period of operating the hand piece exceeds a handicap limit; and
   disabling the hand piece if the number of defective blades found in the time period exceeds a disable limit.

20. The method of claim 19, wherein the data string is an encrypted code and wherein the step of authenticating use of the hand piece comprises the steps of:
   decoding the encrypted code with an encryption algorithm in the console; and
   providing a responding data pattern that can be authenticated.

21. The method of claim 19 further comprising the steps of:
   instructing the hand piece to operate in a handicap mode if a temperature of the hand piece exceeds a handicap limit; and
   disabling the hand piece if the temperature of the hand piece exceeds a disable limit.

22. The method of claim 21 further comprising the step of re-initializing the handicap limit and the disable limit based on varied operational conditions of the hand piece.

23. The method of claim 19 further comprising the steps of:
instructing the hand piece to operate in a handicap mode if a time the hand piece has been active exceeds a handicap limit; and
disabling the hand piece if the number of defective blades found in the time the hand piece has been active exceeds a disable limit.

24. The method of claim 19 further comprising the steps of:
instructing the hand piece to operate in a handicap mode if a number of activations for the hand piece within a time period exceeds a handicap limit; and
disabling the hand piece if the number of activations for the hand piece within the time period exceeds a disable limit.

25. The method of claim 19 further comprising the steps of:
determining whether a reprogram of the console is needed;
reading a reprogram code stored in the memory and reprogramming the console using the reprogram code, if it is determined that a reprogram of the console is needed;
determining whether an upgrade of the console is needed; and
reading an upgrade code stored in the memory and upgrading the console using the upgrade code, if it is determined that an upgrade of the console is needed.

26. The method of claim 19 further comprising the steps of:
reading energy level information stored in the memory; and
driving the hand piece according to a corresponding output displacement;
wherein the energy level information stored in the memory is correlated with corresponding output displacement for driving the hand piece.

27. The method of claim 19 further comprising the steps of:
reading a nominal resonant frequency, a start sweep point and a stop sweep point delimiting a frequency range from the memory;
effecting a frequency sweep in the frequency range; and
detecting a resonant frequency for operating the hand piece.

28. The method of claim 19 further comprising the steps of:
reading a nominal resonant frequency, a bias amount and a margin amount from the memory;
calculating a frequency range based on the nominal resonant frequency, the bias amount and the margin amount;
effecting a frequency sweep in the frequency range; and
detecting a resonant frequency for operating the hand piece.

29. The method of claim 19 further comprising the steps of:
keeping track of a number of uses of the end-effector; and
keeping track of a number of remaining uses allowed for the end-effector.

* * * * *